(12) United States Patent
Tsuchiya

(10) Patent No.: US 6,335,792 B1
(45) Date of Patent: Jan. 1, 2002

(54) METHOD AND APPARATUS FOR MEASURING INTERNAL PROPERTY DISTRIBUTION IN SCATTERING MEDIUM

(75) Inventor: Yutaka Tsuchiya, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 09/716,264

(22) Filed: Nov. 21, 2000

Related U.S. Application Data

(63) Continuation-in-part of application No. PCT/JP99/02696, filed on May 24, 1999.

(30) Foreign Application Priority Data

May 26, 1998 (JP) .......................................... 10-144300

(51) Int. Cl.[7] .......................... G01N 21/00; A61B 5/00
(52) U.S. Cl. ........................ 356/432; 356/343; 600/310; 600/322; 600/473
(58) Field of Search ................................. 356/432, 433, 356/435, 436, 441, 442, 336, 338, 339, 340, 343, 39; 600/310, 316, 322, 323, 328, 339, 473, 476

(56) References Cited

U.S. PATENT DOCUMENTS

| | | | |
|---|---|---|---|
| 5,441,054 A | * 8/1995 | Tsuchiya | ..................... 128/665 |
| 5,477,051 A | * 12/1995 | Tsuchiya | ................. 250/341.1 |
| 5,640,247 A | * 6/1997 | Tsuchiya et al. | ............ 356/446 |
| 5,676,142 A | * 10/1997 | Miwa et al. | ................. 128/633 |
| 5,694,931 A | * 12/1997 | Tsuchiya | ..................... 128/633 |
| 5,772,588 A | * 6/1998 | Miwa et al. | ................. 600/310 |
| 5,836,883 A | * 11/1998 | Tsuchiya et al. | ............ 600/476 |
| 5,983,121 A | * 11/1999 | Tsuchiya | ..................... 600/310 |
| 6,075,610 A | * 6/2000 | Ueda et al. | ................. 356/432 |
| 6,240,305 B1 | * 5/2001 | Tsuchiya | ..................... 600/310 |

OTHER PUBLICATIONS

Progress in Biomedical Optics, vol. 2979 (Japan), The International Biomedical Optics Society, (97), pp. 795–806.
Japanese Journal of Applied Physics, vol. 37, No. 5A, (Japan), The Society of Applied Physics and the Physical Society of Japan, (May 15, 1998), pp. 2717–2723.
Hikari Alliance, vol. 9, No. 11 (Japan), Nippon Kogyo Shuppan (Nov. 1998), pp. 6–8.
The Forward and Inverse Problems in Time Resolved Infra–Red Imaging, S. Arridge, pp. 35–64 (p. 5 of specification).
A Perturbation Approach for Optical Diffusion Tomography Using Continuous–Wave and Time–Resolved Data, R. Barbour et al., pp. 87–120 (p. 5 of specification).
A. Perturbation Approach for Imagining in Dense Scattering Media: Derivation and Evaluation of Imaging Operators, H. Graber et al., pp. 121–143 (p. 5 of specification).

(List continued on next page.)

*Primary Examiner*—Hoa Q. Pham
(74) *Attorney, Agent, or Firm*—Morgan, Lewis & Bockius LLP

(57) ABSTRACT

A method of measuring an internal property distribution of a scattering medium, comprises a step of injecting rays into a measured medium, a step of detecting rays having passed through the interior of the measured medium, a step of acquiring a measurement value of a predetermined parameter for each of combinations of a light injection position with light detection positions, a step of setting a reference value of an absorption coefficient, a step of acquiring an estimate of the parameter for each of the combinations of the light injection position with the light detection positions, a step of computing a weight function in each voxel, based on the Microscopic Beer–Lambert Law, a step of computing a deviation of the absorption coefficient in each voxel, based on the measurement value and estimate of the parameter, and the weight function, and a step of computing an absolute value of the absorption coefficient in each voxel.

20 Claims, 6 Drawing Sheets

OTHER PUBLICATIONS

Photon Hitting Density, J. Schotland et al., Applied Optics, vol. 32, No. 4, (Feb. 1, 1993), pp. 448–453 (p. 66 of specification).

Imaging Diffusive Media Using Time–Independent and Tine–Harmonic Sources: Dependence of Image Quality on Imaging Algorithms, Target Volume, Weight Matrix, and View Angles, J. Change et al., pp. 448–464 (p. 5 of specification).

Initial Assessment of a Simple System for Frequency Domain Diffuse Optical Tomography, B. Pogue et al., pp. 1709–1729 (p. 5 of specification).

Photon–Measurement Density Functions. Part 1: Analytical Forms, S. Arridge, pp. 7395–7409 (pp. 5 and 66 of specification).

Imaging of Multiple Targets in Dense Scattering Media, H. Graber et al., pp. 219–234 (discussed at p. 5 of specification).

Reconstructuring Absorber Images in a Three–Dimensional Scattering Medium by Using Photon–Path Data, A. Maki et al., pp. 299–304 (discussed at p. 5 of specification).

Optical Image Reconstruction Using Frequency–Domain Data: Stimulations and Experiments, H. Jiang et al., pp. 253–266 (p. 6 of specification).

Optical Imaging in Medicine: II. Modelling and Reconstruction, S. Arridge et al., pp. 841–853 (p. 6 of specification).

Tomographic Image Reconstruction from Optical Projections in Light–Diffusing Media, S. Colak et al., pp. 180–213 (p. 6 of specification).

Photon Migration Model for Turbid Biological Medium Having Various Shapes, Y. Tsuchiya et al., pp. 79–81 (p. 7 of specification).

Frequency Domain Analysis of Photon Migration Based on the Microscopic Beer–Lambert Law, Y. Tsuchiya et al., pp. 4848–4851 (p. 7 of specification).

Quantitation of Absorbing Substances in Turbid Media Such as Human Tissues Based on the Microscopic Beer–Lambert Law, Y. Tsuchiya et al., pp. 269–280 (p. 7 of specification).

Quantitation of Absorbers in Turbid Media Using Time Integrated Spectroscopy Based on Microscopic Beer–Lambert Law, H. Zhang et al., pp. 21–22 (p. 7 of specification).

Monte Carlo and Diffusion Calculations of Photon Migration in Non–Infinite Highly Scattering Media, J. Haselgrove et al., pp. 30–41 (p. 66 of specification).

Isotropic Photon Injection for Noninvasive Tissue Spectroscopy, Y. Tsuchiya et al., pp. 2495–2501 (p. 66 of specification).

Time–Resolved Transillumination for Medical Diagnostics, R. Berg et al., pp. 110–119 (p. 72 of specification).

Development of Time Resolved Spectroscopy System for Quantitative Non–Invasive Tissue Measurement, M. Miwa et al., pp. 142–149 (p. 72 of specification).

A Solid Tissue Phantom for Photon Migration Studies, R. Cubeddu et al., pp. 1971–1979 (p. 72 of specification).

Determination of the Optical Properties of Turbid Media from a Single Monte Carlo Simulation, A. Kienle et al., pp. 2221–2227 (pp. 73 and 75 of specification).

* cited by examiner

NEAR-INFRARED ABSORPTION SPECTRA OF
Hb(0.37mM) AND Mb(0.15mM)

ABSOLUTE SPECTRA
SOLID LINES: OXYGENATED
DOTTED LINES: DEOXYGENATED

ABSORPTION SPECTRA OF VARIOUS ORGANISMS

METHOD AND APPARATUS FOR MEASURING INTERNAL PROPERTY DISTRIBUTION IN SCATTERING MEDIUM

RELATED APPLICATION

The present application is a continuation-in-part application of PCT application No. PCT/JP99/02696 filed on May 24, 1999, designating U.S.A. and now pending.

BACKGROUND OF THE INVENTION

1. Field of the Invention

The present invention relates to a method for measuring an internal property distribution in a scattering medium and an apparatus therefor. More specifically, the present invention concerns a measuring method of internal property distribution and is applicable to equipment for obtaining internal information while moving a light injection position and a light detection position along a surface of a measured object, and an apparatus therefor.

2. Related Background Art

Optical CT (computer tomography) means a technique or apparatus of measuring an optical property distribution or a concentration distribution of an absorptive constituent in an organism, and makes use of light (signal light) detected after injection of light into a living tissue and migration therethrough.

Three types of optical CT techniques making use of rectilinearly propagating light, quasi-rectilinearly propagating light, and scattered light have been reported heretofore. Among these, the method making use of rectilinearly propagating light has extremely poor utilization efficiency of light and is thus applicable only to very small media. For example, where the near-infrared light is used, transmitted light demonstrates attenuation to about $10^{-5}$ times against a standard living tissue having the thickness of 1 cm. In contrast with it, the method making use of scattered light utilizes all light emerging from the medium, so as to increase signal-to-noise ratios, and is thus expected to be applied to larger media. The method making use of quasi-rectilinearly propagating light stands intermediate between these two methods.

The practical optical CT needs to utilize the scattered light because of the limitations including maximum permissible incidence power to organisms, measurement sensitivity, required measurement time, and so on, but the above optical CT does not have been put into practical use yet because of the following technological problems.

The first problem is that no method has been developed for describing the behavior of light or a photon in a scattering medium with sufficient accuracy. For analyzing the behavior of a photon migrating in a scattering medium, it has been common practice heretofore to employ approximation to the transport equation, or the photon diffusion equation resulting from application of diffusion approximation to the transport theory. The diffusion approximation, however, holds only in sufficiently larger media than the mean free path length of photons therein and is thus incapable of handling relatively small media, tissues having complicated internal shapes, and media having complicated shapes. In addition, the diffusion approximation is predicated on isotropic scattering; therefore, when applied to measurement of actual living tissues having anisotropic scattering characteristics, it gives rise to unignorable errors due to the anisotropic scattering. Further, the diffusion equation does not allow us to find its solution by either of analytical or numerical techniques (such as the finite element method or the like) unless boundary conditions are preliminarily set. Namely, it is necessary to set the boundary conditions at each of the light injection and detection positions, i.e., the shape of the medium and reflection characteristics at interfaces, prior to measurement. If these conditions vary depending upon individual differences etc., computation must be redone under boundary conditions modified according to the variation. Therefore, the optical CT making use of the relation between signal light and optical properties of a scattering medium derived from the approximate expression of the transport equation or the photon diffusion equation still has a significant problem in accuracy and operability.

Besides the above, there is another method for deriving the relation between signal light and optical properties of a scattering medium by applying the perturbation theory to the approximate expression of the transport equation or to the photon diffusion equation, and for reconstructing an optical CT image using this relation. This method, however, makes how to handle its nonlinear effects (terms of the second and higher degrees) very complex. On this occasion, it is theoretically possible to perform the computation including the terms of the second and higher degrees by a computer, but operation time is enormous even with use of the presently fastest computer; therefore, practical use thereof is impossible. It is thus usual practice to ignore the terms of the second and higher degrees. Therefore, when this method is applied to reconstruction of an optical CT image of a medium containing a plurality of relatively strong absorption regions, interaction becomes unignorable between the absorption regions and a large error can be made due to it.

The second problem is that the conventional optical CT makes use of a weight function in a narrow sense, i.e., a mean path length or a phase lag equivalent thereto. For this reason, it becomes extremely complicated to handle the mean path length of detected light varying depending upon absorption coefficients. It is thus usual practice to employ approximation, but use of approximation poses a significant problem of increase in errors. Such methods making use of the weight function in a narrow sense are described, for example, in references listed below. (1) S. Arridge: SPIE Institutes for Advanced Optical Technologies, Vol. IS11, Medical Optical Tomography: Functional Imaging and Monitoring, 35–64 (1993); (2) R. L. Barbour and H. L. Graber: ibid. 87–120 (1993); (3) H. L. Graber, J. Chang, R. Aronson and R. L. Barbour: ibid. 121–143 (1993); (4) J. C. Schotland, J. C. Haselgrove and J. S. Leigh: Applied optics, 32, 448–5453 (1993); (5) Chang, R. Aronson, H. L. Graber and R. L. Barbour: Proc. SPIE, 2389, 448–464 (1995); (6) B. W. Pogue, M. S. Patterson, H. Jiang and K. D. Paulsen: Phys. Med. Biol. 40, 1709–1729 (1995); (7) S. R. Arridge: Applied Optics, 34, 7395–7409 (1995); (8) H. L. Graber, J. Chang, and R. L. Barbour: Proc. SPIE, 2570, 219–234 (1995); (9) A. Maki and H. Koizumi: OSA TOPS, Vol. 2, 299–304 (1996); (10) H. Jiang, K. D. Paulsen and Ulf L. Osterberg: J. Opt. Soc. Am. A13, 253–266 (1996); (11) S. R. Arridge and J. C. Hebden: Phys. Med. Biol. 42, 841–853 (1997); (12) S. B. Colak, D. G. Papaioannou, G. W. It Hooft, M. B. van der Mark, H. Schomberg, J. C. J. Paasschens, J. B. M. Melissen and N. A. A. J. van Astten: Applied Optics, 36, 180–213 (1997).

In image reconstruction of optical CT, it is most important to know which part the signal light has passed in the scattering medium, i.e., to know a path distribution of the signal light in the medium. From this viewpoint, there is also a method for deriving the path distribution of signal light by the random walk theory or the like, but the aforementioned problem is not solved yet.

As described above, the conventional optical CT techniques do not allow us to obtain a reconstructed image with sufficient accuracy and still have significant issues in terms of spatial resolution, image distortion, quantitation, measurement sensitivity, required measurement time, and so on.

In order to break through the circumstances as described above, the inventors have been conducting a series of studies with the focus on the following points. Namely, the important points for realizing optical CT are to clarify the behavior of light migrating in living tissues of strong scattering media, to clarify the relation between signal light detected and optical properties of scattering media (scattering absorbers) containing absorptive constituents, and to develop an algorithm for reconstructing an optical CT image by making use of the signal light and the relation.

Then the inventors proposed ① a model based on Microscopic Beer-Lambert Law (hereinafter referred to as "MBL"), derived ② analytic expressions to indicate the relation between optical properties of scattering media and signal light, and reported them in the following references, for example. (13) Y. Tsuchiya and T. Urakami: Jpn. J. Appl. Phys. 34, L79–81 (1995); (14) Y. Tsuchiya and T. Urakami: Jpn. J. Appl. Phys. 35, 4848–4851 (1996); (15) Y. Tsuchiya and Urakami: Optics Communications, 144, 269–280 (1997); (16) H. Zhang, M. Miwa, Y. Yamashita and Y. Tsuchiya: Ext. Abstr. Optics Japan '97, 30aA08 (1997). From the principle, this MBL-based method has a significant feature of being free of influence of the medium shape, boundary conditions, and scattering and thus is also applicable to anisotropic scattering media and small media. As a consequence, the method clarified the photon migration in scattering media and made it possible to measure absorption coefficients of scattering media or concentrations of absorbers, based on this theory.

SUMMARY OF THE INVENTION

The inventors, however, found that neither of the above conventional methods was readily applicable to inhomogeneous systems, because they made use of the conventional weight function in a narrow sense, and that the measurement accuracy was not sufficient yet for the absorptive constituents in the scattering media such as organisms.

The present invention has been accomplished in view of the above conventional issues and an object of the invention is to provide a method and an apparatus that permit measurement of an absorptive constituent with higher accuracy even when applied to the scattering media of inhomogeneous systems such as organisms or the like.

As a result of extensive and intensive research in order to achieve the above object, the inventors further developed the above knowledge found by the inventor, and discovered that the above object was accomplished by ③ applying the aforementioned MBL to the inhomogeneous systems, ④ deriving analytic expressions to indicate the relation between optical properties of inhomogeneous scattering media and signal light, ⑤ deriving a weight function according to a different definition from the conventional one from the relation between signal light and optical properties of inhomogeneous scattering media, and ⑥ providing an algorithm and an apparatus for reconstructing an optical CT image by use of this weight function, whereby the inventors reached the invention.

Namely, a method for measuring an internal property distribution of a scattering medium according to the present invention is a method comprising:

a light injection step of successively injecting rays from at least one light injection position into a medium to be measured, which is a scattering medium;

a light detection step of detecting rays having passed through the interior of the medium to be measured, at a plurality of light detection positions;

a measurement value acquisition step of acquiring a measurement value of a predetermined parameter of the rays for each of combinations of the light injection position with the light detection positions, based on each ray detected;

a reference value setting step of setting a reference value of an absorption coefficient of the medium to be measured;

an estimate computation step of computing an estimate of said parameter for each of the combinations of the light injection position with the light detection positions, based on the reference value of the absorption coefficient, on the assumption that the medium to be measured has the homogeneous reference value of the absorption coefficient as a whole;

a weight function operation step of obtaining a weight function in each voxel of the medium to be measured, the medium being divided into a plurality of voxels, based on the Microscopic Beer-Lambert Law, using the reference value of the homogeneous absorption coefficient;

an absorption coefficient deviation computation step of computing a deviation of the absorption coefficient from the reference value of the absorption coefficient in each voxel, based on the measurement value of the parameter, the estimate of the parameter, and the weight function; and an absorption coefficient absolute value computation step of computing an absolute value of the absorption coefficient in each voxel, based on the reference value of the absorption coefficient and the deviation of the absorption coefficient, to obtain a distribution of absolute values of absorption coefficients in the medium to be measured.

An apparatus for measuring an internal property distribution of a scattering medium according to the present invention is an apparatus comprising:

light injection means for successively injecting rays from at least one light injection position into a medium to be measured, which is a scattering medium;

light detection means for detecting rays having passed through the interior of the medium to be measured, at a plurality of light detection positions;

measurement value acquisition means for acquiring a measurement value of a predetermined parameter of the rays for each of combinations of the light injection position with the light detection positions, based on each ray detected;

reference value setting means for setting a reference value of an absorption coefficient of the medium to be measured;

estimate computation means for computing an estimate of the parameter for each of the combinations of the light injection position with the light detection positions, based on the reference value of the absorption coefficient, on the assumption that the medium to be measured has the homogeneous reference value of the absorption coefficient as a whole;

weight function operation means for obtaining a weight function in each voxel of the medium to be measured, the medium being divided into a plurality of voxels, based on the Microscopic Beer-Lambert Law, using the homogeneous reference value of the absorption coefficient;

absorption coefficient deviation computation means for computing a deviation of the absorption coefficient from the reference value of the absorption coefficient in each voxel, based on the measurement value of the parameter, the estimate of the parameter, and the weight function; and absorption coefficient absolute value computation means for computing an absolute value of the absorption coefficient in each voxel, based on the reference value of the absorption coefficient and the deviation of the absorption coefficient, to obtain a distribution of absolute values of absorption coefficients in the medium to be measured.

In the method and apparatus of the present invention, in each measurement the weight function in each voxel, which is first disclosed by the present invention, is directly gained based on the MBL, and the deviation of the absorption coefficient in each voxel is computed based on the weight function, the measurement value of the predetermined parameter, and the estimate of the parameter. On this occasion, the weight function is expressed by an equation of one kind regardless of the measurement circumstances. Since in the present invention the deviation of the absorption coefficient is computed based on the appropriate weight function even with variations in the individual measurement circumstances as described above, the invention prevents errors from being caused by employment of the approximation. For this reason, even in cases where the method and apparatus of the present invention are applied to the scattering media of inhomogeneous systems such as organisms or the like, they allow the deviation of the absorption coefficient in each voxel to be computed accurately, and improve the measurement accuracy of the internal property distribution (optical CT image) obtained based on such absorption coefficient deviation.

A preferred weight function adopted in the above method and apparatus of the present invention is a function of the mean path length in each voxel and the variance of the distribution of path lengths, on the assumption that the medium to be measured has the homogeneous reference value of the absorption coefficient as a whole.

In this case, it is preferable that the method (or the apparatus) further comprise the mean path length acquisition step (or the mean path length acquisition means) of acquiring the mean path length in each voxel, based on the reference value of the absorption coefficient, on the assumption that the medium to be measured has the homogeneous reference value of the absorption coefficient as a whole, and that the aforementioned weight function operation step comprise (or the weight function operation means perform) a step of gaining the weight function, based on the following equation:

$$W_i = Z_i(\mu_{av}) - (\Delta\mu_{ai}/2)\sigma_{iv}^2 \qquad (1)$$

[where $W_i$ is the weight function, $Z_i(\mu_{av})$ the mean path length, $\Delta\mu_{ai}$ the deviation of the absorption coefficient, and $\sigma_{iv}^2$ the variance of the distribution of path lengths].

Another preferred weight function adopted in the above method and apparatus of the present invention is a function of the mean path length in a predetermined time domain in each voxel and a variance of a distribution of path lengths, on the assumption that the medium to be measured has the homogeneous reference value of the absorption coefficient as a whole.

In this case, it is preferable that the method (or the apparatus) further comprise the mean path length acquisition step (or the mean path length acquisition means) of obtaining the mean path length in a predetermined time domain in each voxel, based on the reference value of the absorption coefficient, on the assumption that the medium to be measured has the homogeneous reference value of the absorption coefficient as a whole, and that the aforementioned weight function operation step comprise (or the weight function operation means perform) a step of gaining the weight function, based on the following equation:

$$W_i = Z_i(\mu_{av}) - (\Delta\mu_{ai}/2)\sigma_{iv}^2 \qquad (1)$$

[where $W_i$ is the weight function, $Z_i(\mu_{av})$ the mean path length, $\Delta\mu_{ai}$ the deviation of the absorption coefficient, and $\sigma_{iv}^2$ the variance of the distribution of path lengths].

Further, still another preferred weight function adopted in the above method and apparatus of the present invention is a function of a group delay in each voxel and a variance of a distribution thereof, on the assumption that the medium to be measured has the homogeneous reference value of the absorption coefficient as a whole.

In this case, it is preferable that the method (or the apparatus) further comprise a group delay acquisition step (or group delay acquisition means) of acquiring a group delay in each voxel, based on the reference value of the absorption coefficient, on the assumption that the medium to be measured has the homogeneous reference value of the absorption coefficient as a whole, and that the aforementioned weight function operation step comprise (or the weight function operation means perform) a step of gaining the weight function, based on the following equation:

$$W_i = c \left.\frac{\partial \phi_i}{\partial \omega}\right|_{\mu_{av}} - \frac{\Delta\mu_{ai}}{2}\sigma_f^2 \qquad (2)$$

[where $W_i$ is the weight function, $$c \left.\frac{\partial \phi_i}{\partial \omega}\right|_{\mu_{av}}$$

is c (speed of light in the medium) times the group delay, $\Delta\mu_{ai}$ the deviation of the absorption coefficient, and $\sigma_f^2$ the variance of a distribution].

With adoption of the preferred weight functions in the method and apparatus of the present invention as described above, because the weight functions are computed in consideration of not only the mean path length or the group delay varying depending upon the absorption coefficient, but also the variance of distribution thereof, there is a tendency to attain further improvement in the measurement accuracy of the internal property distribution obtained by use of such weight functions.

The method and apparatus of the present invention may further comprise a concentration computation step (or concentration computation means) of computing a concentration of an absorptive constituent in each voxel by using the absolute value of the absorption coefficient, and thus obtaining a concentration distribution of the absorption constituent in the medium to be measured. Since concentrations of the absorptive constituent can be obtained based on the absorption coefficient deviations determined accurately as described above by such method and apparatus, the concentration distribution can be obtained with high accuracy.

In the cases where the method and apparatus of the present invention are applied to a measured medium containing at least two absorptive constituents, it is preferable that the rays injected into the measured medium in the light injection step (light injection means) have at least two wavelengths at which said absorptive constituents demonstrate their respective absorption coefficients different from each other. In this case, each of the rays having the at least two wavelengths is detected in the light detection step (or by the light detection means), the measurement value is acquired as to each of the rays having the at least two wavelengths in the measurement value acquisition step (or by the measurement value acquisition means), the reference value is set as to each of the rays having the at least two wavelengths in the reference value setting step (or by the reference value setting means), the estimate is computed as to each of the rays having the at least two wavelengths in the estimate computation step (or by the estimate computation means), the weight function is gained as to each of the rays having the at least two wavelengths in the weight function operation step (or by the weight function operation means), the deviation of the absorption coefficient is computed as to each of the rays having the at least two wavelengths in the absorption coefficient deviation computation step (or by the absorption coefficient deviation computation means), the absolute value of the absorption coefficient is computed as to each of the rays having the at least two wavelengths in the absorption coefficient absolute value computation step (or by the absorption coefficient absolute value computation means), and concentrations of each absorptive constituent are computed as to each of the rays having the at least two wavelengths in the concentration computation step (or by the concentration computation means), thereby obtaining a concentration distribution of each of the absorption constituents in the measured medium.

The method and apparatus of the present invention described above may further comprise an image display step (or image display means) of displaying an optical CT image to indicate the distribution in the measured medium, based on the aforementioned distribution obtained. The method and apparatus of the present invention in this structure can display the optical CT image with high accuracy by imaging of the internal property distribution obtained with accuracy as described above.

DESCRIPTION OF THE PREFERRED EMBODIMENTS

Figure 1:
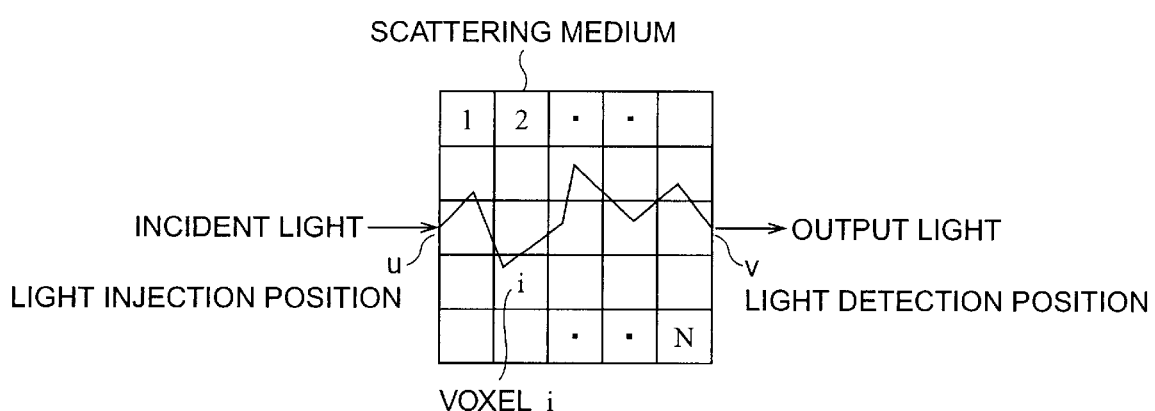
FIG. 1 is a schematic diagram to show a model concerning photon migration in an inhomogeneous medium.

The principles and preferred embodiments of the present invention will be described below in detail with reference to the drawings. It is noted here that in the drawings identical or equivalent portions will be denoted by identical reference symbols. Although a ray traveling while being scattered needs to be discussed using three-dimensional coordinates, it will be described using two-dimensional coordinates in certain cases for simplification of description. First, the principles of the present invention will be described.

PRINCIPLES OF THE PRESENT INVENTION

The present invention employs novel weight functions derived based on the Microscopic Beer-Lambert Law. Namely, the weight functions according to the present invention are different from the conventional weight functions, i.e., from photon path lengths and the mean path length in each voxel (volume element), photon residence time, phase delays corresponding thereto, and so on. The weight functions adopted in the present invention are expressed in the from involving the medium shape, the boundary conditions, the light incidence and detection positions, the distance between them, the scattering coefficient of the medium, and so on. These weight functions are uniquely determined against a scattering medium. Since in the present invention the optical CT image is reconstructed using the weight functions as described above, the errors, which were the problem heretofore, are reduced greatly as described hereinafter, whereby the optical CT image can be obtained with high accuracy.

1. Photon Migration Model

First described is a model of photon migration in a scattering medium, which is the fundamentals of the present invention.

A) The scattering medium has an arbitrary three-dimensional shape that never permits reentry of emergent light. Therefore, no photon emerging from the medium is incident again into the medium. Within this restriction, the boundary conditions between the scattering medium and an external medium, for example, matching conditions of shape and refractive index, can be determined on an optional basis.

B) In the scattering medium there is no nonlinear action between photons and the medium and no interaction between photons. Therefore, the optical constants of the medium are independent of photon density.

C) Macroscopic refracting properties are uniform (homogeneous). However, absorption coefficient distribution is not uniform (inhomogeneous). Such a medium will be called hereinafter an inhomogeneous medium or an inhomogeneous system for convenience sake. Therefore, the speed of light in the scattering medium, discussed below, is a constant c.

D) When light injection-detection positions p(u, v) (to inject photons at a surface position u and detect scattered photons at another surface position v) are set for the above inhomogeneous scattering medium, a photon path distribution ($\mu_a=0$) thereof is determined uniquely. This photon path distribution ($\mu_a=0$) is a distribution of potential photon paths or a distribution of potential photon path lengths on the assumption that no absorption occurs in the scattering medium. This scattering medium assumed to absorb no photon is called an "imaginary medium."

E) The above photon path distribution ($\mu_a=0$) is not affected by absorption or absorption distribution of the scattering medium, because it is defined for the imaginary medium assumed to be the scattering medium without absorption. This photon path distribution ($\mu_a=0$) is dependent on the scattering property of the scattering medium, the shape of the medium, the boundary conditions, and the light injection-detection positions p(u, v). Effects of these are included in the photon path distribution ($\mu_a=0$). Namely, since the effects of scattering etc. are reflected by the photon path distribution ($\mu_a=0$) for the imaginary medium without absorption, the photon path distribution ($\mu_a=0$) and a response to the imaginary medium with $\mu_a=0$ will be sometimes called hereinafter simply the effects of scattering etc.

F) In connection with the aforementioned item B), the above photon path distribution ($\mu_a=0$) is invariant against injection of a plurality or a lot of photons (photon assemblage) and against migration of many photons.

It is also noted that the following relations hold as to the photon migration and attenuation in the medium:

G) a relation that an attenuation is $\mu_a l$ where a single photon migrates by a photon path length $l=ct$ in a homogeneous medium with the absorption coefficient of $\mu_a$ (this relation will be called "MBL first basic rule"); and H) a relation that an attenuation for many photons (photon assemblage) in the scattering medium is expressed by superposition of attenuations of the respective photons.

2. Fundamentals Concerning Photon Migration in Inhomogeneous System

The fundamentals concerning the photon migration in the inhomogeneous system will be described first.

2.1 Photon migration in inhomogeneous medium

The whole three-dimensional inhomogeneous medium having the inhomogeneous distribution of absorption (or an absorptive constituent) is divided into N voxels, a number i is assigned to each voxel, and an anisotropic scattering coefficient $\mu_s$, a mean cosine of scattering angles g, and an absorption coefficient $\mu_{ai}$ are defined for each voxel i (reference is made to FIG. 1). The photon injection-detection positions are p(u, v). Here $\mu_s$ and $\mu_{ai}$ are values inherent in the inhomogeneous medium, $\mu_s$ is a constant, and $\mu_{ai}$ is a function of position. On this occasion, the voxel i may have arbitrary size and shape and a voxel of a large volume can be handled noting an average absorption coefficient or the mean path length in that voxel. Further, two or more voxels spatially apart from each other may also be considered together as one voxel.

Now let us consider a case of repetitive injection of single photons and an output $h_m(t)$ detected at a time t against the m-th injected photon (m-th photon). Let $t_{im}$ be a time of residence (or flight) of this m-th photon in the voxel i and $l_{im}$ ($=ct_{im}$) be a corresponding path length. In this case, the relation between the path length l of the detected photon and $l_{im}$ is given by $l=ct=\Sigma l_{im}$. Here the subscript m represents an amount concerning the m-th photon. When the photon path of the m-th photon, i.e., the photon path distribution ($\mu_a=0$), is determined in the above system, $l_{im}$ is determined uniquely. When the voxel number i is determined, the absorption coefficient $\mu_{ai}$ of that voxel i is determined uniquely. In this case, because the absorption coefficient is under optional selection, the photon path length and absorption coefficient of voxel are independent of each other.

The attenuation (which is also called an extinction amount) $B_m$ of the m-th photon detected at the time t is given by the following equation.

$$B_m = \sum_{i=1}^{N} (\mu_{ai} l_{im}) \quad (2.1.1)$$

However, for each voxel i through which no photon has passed, $l_{im}=0$, i.e., $t_{im}=0$ is defined (i.e., the path length distribution thereof is zero). Therefore, $B_m$ in Eq. (2.1.1) includes no effects of the voxels through which no photon has passed. Since $\mu_{ai}$ and $l_{im}$ are both nonnegative values, $B_m=\Sigma(\mu_{ai}l_{im})=0$ is met only when the absorption coefficients $\mu_{ai}$ of the voxels i of $l_{im}\neq 0$ are equal to zero. On this occasion, since Eq. (2.1.1) includes no effects of the voxels of $l_{im}=0$, the condition of $\Sigma(\mu_{ai}l_{im})=0$ can be replaced by $\Sigma\mu_{ai}=0$.

This Eq. (2.1.1) indicates the MBL first basic rule in the inhomogeneous system, i.e., that "the attenuation of a photon having migrated by the length $l=\Sigma l_{im}$ along a zigzag photon path in the scattering medium having the absorption coefficients $\mu_{ai}$ is the value $\Sigma(\mu_{ai}l_{im})$ independent of the scattering property of the medium." This relation represents connection of MBL at the positions of change in the absorption coefficients during the photon migration. This relation also holds when the zigzag photon path makes intersections (where the photon passes the same place two or more times).

Now let $s_m(\mu_s, t)$ be a response to the m-th photon when $\Sigma\mu_{ai}=0$. Then a response $h_m(t)$ to the m-th photon is given by the following equation.

$$\ln h_m(t) = \ln s_m(\mu_s, t) - \sum_{i=1}^{N}(\mu_{ai}l_{im}) \quad (2.1.2)$$

Since the path length and absorption coefficient of each voxel are independent, we can obtain the following relation.

$$\frac{\partial \ln h_m(t)}{\partial \mu_{ai}} = -\frac{\partial B_m}{\partial \mu_{ai}} = -\frac{\partial B_{im}}{\partial \mu_{ai}} = -l_{im} \quad (2.1.3)$$

However, $B_{im}$ in the above equation is the attenuation in the voxel i. This Eq. (2.1.3) represents the MBL concerning the m-th photon in the inhomogeneous system.

Then we can obtain the following relations for the m-th photon in the inhomogeneous system from Eq. (2.1.3).

$$\ln h_m(t) = \ln s_m(\mu_s, t) - \sum_{i=1}^{N} \int_0^{\mu_{ai}} l_{im} d\mu_a \quad (2.1.4)$$

$$= \ln s_m(\mu_s, t) - \sum_{i=1}^{N}(\mu_{ai}l_{im})$$

$$h_m(t) = s_m(\mu_s, t)\exp\left[-\sum_{i=1}^{N}\int_0^{\mu_{ai}} l_{im} d\mu_a\right] \quad (2.1.5)$$

$$= s_m(\mu_s, t)\exp\left[-\sum_{i=1}^{N}(\mu_{ai}l_{im})\right]$$

Let us consider photons having the photon path length of l out of photons constituting a response obtained when a lot of photons (photon assemblage) are injected into the inhomogeneous medium. In this case, there exist as many photon paths having the path length of l in the medium as infinite. The attenuation for many photons (photon assemblage) is expressed by superposition of attenuations of single photons. An ordinary response, for example, an impulse response, includes photons of different path lengths. In this case, the attenuation can also be expressed by superposition of attenuations of single photons. The photon path distribution ($\mu_a=0$) defined previously is invariant against injection of many photons. Therefore, attenuations of various responses of the inhomogeneous system against injection of many photons can be analyzed as superposition of attenuations of single photons, i.e., as a linear problem.

2.2 Photon Path Distribution ($\mu_a=0$) of Inhomogeneous medium

When the light injection-detection positions p(u, v) are set for any given inhomogeneous medium that never permits reentry of emergent light, the photon path distribution available for photons is determined uniquely. Since this photon path distribution ($\mu_a=0$) is defined by the photon path distribution (of the imaginary medium, $\mu_a=0$) based on the assumption that the inhomogeneous medium absorbs no photon ($\mu_a=0$), it is not affected by absorption and distribution thereof in the inhomogeneous medium. However, the photon path distribution ($\mu_a=0$) is dependent upon the optical properties of the inhomogeneous medium, the shape of the medium, the boundary conditions, the light injection-detection positions p(u, v), and the path length.

The photon path distribution ($\mu_a=0$) can be defined for each of photon assemblages constituting an impulse response to the inhomogeneous system, a time-resolved gate integration signal of the impulse response, and a response in the frequency domain. Once the photon path distribution ($\mu_a=0$) is determined, a mean path length ($\mu_a=0$) of each voxel will be determined uniquely.

The photon path distributions ($\mu_a=0$) as described above can be computed by Monte Carlo simulations or the like. Further, the Monte Carlo simulations also allow us to compute the photon path distribution and mean path length of detected light under the condition of presence of arbitrary and uniform absorption (for example, $\mu_a=\mu_{av}$), based on the photon path distribution ($\mu_a=0$).

2.3 Photon Path Distribution of Detected Light

An impulse response includes photons having various path lengths. When the medium involves absorption, the attenuation of individual photons is given by $B_m=\Sigma(\mu_{ai}l_{im})$, and the mean path length of an assemblage of photons having different path lengths is expressed by a function of absorption coefficient. The time waveform of the response thus varies depending upon absorption. Namely, with presence of absorption, photons become extinct midway during the photon migration, degrees of the extinction differ depending upon the photon path length or photon path distribution ($\mu_a=0$), and thus the mean path length and photon path distribution for detected light vary by the degrees. As a consequence, the photon path distribution of detected light is normally dependent upon absorption and is not equal to the aforementioned photon path distribution ($\mu_a=0$).

2.4 Weight Functions

An attenuation of a single photon having migrated by l in the inhomogeneous medium is expressed by $\Sigma(\mu_{ai}l_{im})$ as described previously. Then an attenuation of many photons in the inhomogeneous medium is expressed by superposition of attenuations of single photons. Let us consider here an attempt to express attenuations of various responses of inhomogeneous medium comprised of multiple photons by the product of contribution coefficient $W_i$ in the voxel i and absorption coefficient $\mu_{ai}$ of the voxel i. Then this contribution coefficient $W_i$ is called a "weight function."

In the case of aforementioned Eq. (2.1.4) and Eq. (2.1.5), since the path length $l=ct=\Sigma l_{im}$ is not a function of absorption coefficient $\mu_{ai}$, the photon path distribution ($\mu_a=0$) is equivalent to the weight functions. However, in the cases where the mean path length is a function of absorption coefficient as in the case of time integral of an impulse response, the weight functions are not equal to the photon path distribution ($\mu_a=0$) or to the photon path distribution of detected light, as described hereinafter. In general, the weight functions $W_i$ are dependent upon absorption.

3. Various Response Functions in Inhomogeneous System

With the above in mind, the MBL for the inhomogeneous system will be derived by obtaining various responses in the inhomogeneous system. On this occasion, the light injection-detection positions are set as p(u, v) for the inhomogeneous medium. Then the photon path distribution ($\mu_a=0$) is determined uniquely for each of the various responses obtained by various measurements in the time domain and in the frequency domain. An attenuation of each of the various responses is superposition of attenuations of single photons constituting each of the various responses. Since the photon path distribution ($\mu_a=0$) is invariant against absorption distribution, the same photon path distribution ($\mu_a=0$) is yielded, regardless of whether the medium to be measured is an inhomogeneous medium or a homogeneous medium, as long as setting of the measurement system, i.e., the light injection-detection positions p(u, v) and the measurement method, is the same. The description and analysis methods based on the MBL are excellent in that they can describe the response under $\mu_a=0$ (i.e., the effects of scattering and boundary conditions) and the attenuation due to absorption in separate terms even in the case of responses of the inhomogeneous system.

3.1 Impulse Response of Inhomogeneous System

The impulse response h(t) of the inhomogeneous system is comprised of a lot of detected photons having various path lengths. In this case, once the observation time t is determined, the path length l will be determined by l=ct. Let us suppose that the number M of detected photons having the path length of l is sufficiently large. In this case, since the path length $l_m$ of all photons is equal to l, the mean path length for the M photons is also l, i.e., the following relation holds.

$$\frac{1}{M}\sum_{m=1}^{M} l_m = l \qquad (3.1.1)$$

The photon path distribution ($\mu_a=0$) of such a photon assemblage having the path length of l is determined uniquely against the shape of the medium, the scattering property, and the light injection-detection positions p(u, v), and is irrelevant to the absorption coefficient and absorption distribution of the inhomogeneous medium. Then, considering a sufficiently large number, M, of photons (photon assemblage) having the path length of l against the impulse response under $\mu_a=0$, the photon path distribution ($\mu_a=0$) of this photon assemblage is expressed by the mean path length $l_i$ ($\mu_a=0$) of each voxel i (i=1 to N). With reference to Eq. (3.1.1), the following relation holds as to this mean path length $l_i$.

$$\sum_{i=1}^{N} l_i = \sum_{i=1}^{N}\left(\frac{1}{M}\sum_{m=1}^{M} l_{im}\right) = \frac{1}{M}\sum_{m=1}^{M}\left(\sum_{i=1}^{N} l_{im}\right) = l \qquad (3.1.2)$$

Namely, the summation of mean path lengths $l_i$ of multiple photons in the respective voxels over all the voxels is equal to the mean path length l of the multiple photons.

The following equations give the attenuation $B_h$ of the photon assemblage having the path length of l out of the (plurality of) photons constituting the impulse response, and the attenuation $B_{ih}$ in the voxel i.

$$B_h = \sum_{i=1}^{N} (\mu_{ai} l_i) = \sum_{i=1}^{N} B_{ih} \qquad (3.1.3)$$

$$B_{ih} = \mu_{ai} l_i \qquad (3.1.4)$$

Therefore, where the impulse response under $\Sigma\mu_{ai}=0$ is defined as $s(\mu_s, t)$, the impulse response h(t) of the inhomogeneous system is expressed as follows.

$$\ln h(t) = \ln s(\mu_s, t) - B_h = \ln s(\mu_s, t) - \sum_{i=1}^{N}(\mu_{ai}l_i) \quad (3.1.5)$$

Then we can obtain the MBL for the impulse response of the inhomogeneous system, i.e., the following relation.

$$\frac{\partial \ln h(t)}{\partial \mu_{ai}} = -\frac{\partial B_h}{\partial \mu_{ai}} = -\frac{\partial B_{ih}}{\partial \mu_{ai}} = -l_i \quad (3.1.6)$$

From the above, the impulse response h(t) of the inhomogeneous system is given as follows.

$$\ln h(t) = \ln s(\mu_s, t) - \sum_{i=1}^{N}\int_0^{\mu_{ai}} l_i d\mu_a \quad (3.1.7)$$

$$= \ln s(\mu_s, t) - \sum_{i=1}^{N}(\mu_{ai}l_i)$$

$$h(t) = s(\mu_s, t)\exp\left[-\sum_{i=1}^{N}\int_0^{\mu_{ai}} l_i d\mu_a\right] \quad (3.1.8)$$

$$= s(\mu_s, t)\exp\left[-\sum_{i=1}^{N}(\mu_{ai}l_i)\right]$$

In these equations, the impulse response under $\mu_a=0$, i.e., the term $s(\mu_s, t)$ to indicate the effects of the medium shape and scattering, is separated from the term $B_h$ to indicate the attenuation dependent upon absorption, as stated previously.

It is seen from above Eq. (3.1.7) that the weight functions for the impulse response h(t) of the inhomogeneous system are equal to the path lengths $l_i$ ($\mu_a=0$) of the voxels i (i=1 to N) determined by the photon path distribution ($\mu_a=0$) defined previously. Therefore, an algorithm for reconstructing the optical CT image by time-resolved measurement becomes relatively easier.

In the following, various responses and weight functions therefor will be derived using the photon path distribution ($\mu_a=0$) of the photon assemblage constituting the impulse response h(t) of the inhomogeneous system obtained above, i.e., the path lengths $l_i$ ($\mu_a=0$) of the voxels defined previously, or their temporal distribution ($l_i$ ($\mu_a=0$) against 1 ($\mu_a=0$) taking different values, which will be called a time-resolved photon path distribution ($\mu_a=0$)).

3.2 Time-resolved Gate Integration Signal of Impulse Response of Inhomogeneous System In this section, analytic equations will be first derived for the time-resolved gate integration signal of the impulse response of the inhomogeneous system and then the weight functions will be derived taking account of absorption dependency of attenuation and mean path length. When the integration range of time domain $[t_1, t_2]$ is set to $[0, \infty]$, the response represents one to stationary (CW) light.

3.2.1 Analytic equations of time-resolved gate integration signal

The time-resolved gate integration signal $I_T$ of the impulse response is expressed below as a result of integration of Eq. (3.1.8).

$$I_T = \int_{t_1}^{t_2} h(t)dt = \int_{t_1}^{t_2} s(\mu_s, t)\exp\left[-\sum_{i=1}^{N}\int_0^{\mu_{ai}} l_i d\mu_a\right]dt \quad (3.2.1)$$

$$= \int_{t_1}^{t_2} s(\mu_s, t)\exp\left[-\sum_{i=1}^{N}(\mu_{ai}l_i)\right]dt$$

From this equation, we can obtain the following equation.

$$\frac{\partial \ln I_T}{\partial \mu_{ai}} = \frac{1}{I_T}\frac{\partial I_T}{\partial \mu_{ai}} \quad (3.2.2)$$

$$= \frac{\int_{t_1}^{t_2} l_i s(\mu_s, t)\exp\left[-\sum_{i=1}^{N}(\mu_{ai}l_i)\right]dt}{\int_{t_1}^{t_2} s(\mu_s, t)\exp\left[-\sum_{i=1}^{N}(\mu_{ai}l_i)\right]dt}$$

$$= -\langle l_{iT}\rangle = -L_i(\mu_a)$$

In this equation $\langle l_{iT}\rangle = L_i(\mu_a)$ represents the mean path length of the voxel i against the time-resolved gate integration signal of the impulse response. This $L_i(\mu_a)$ is dependent upon the scattering property of the medium, the boundary conditions, and $t_1$, $t_2$. As seen from Eq. (3.2.9) described hereinafter, $L_i(\mu_a)$ is a monotone non-increasing function against $\mu_{ai}$. Further, above $L_i(\mu_a)$ is a function of the absorption coefficient of the voxel i, and is also a function of the absorption coefficients $\mu_{ai}$ of all the voxels i (i=1 to N) including the voxel i. This dependency of $L_i(\mu_a)$ on absorption of all voxels will be described hereinafter.

Then we can gain the following equation from Eq. (3.2.2).

$$\sum_{i=1}^{N} L_i(\mu_a) = \frac{\sum_{i=1}^{N}\int_{t_1}^{t_2} l_i s(\mu_s, t)\exp\left[-\sum_{i=1}^{N}(\mu_{ai}l_i)\right]dt}{\int_{t_1}^{t_2} s(\mu_s, t)\exp\left[-\sum_{i=1}^{N}(\mu_{ai}l_i)\right]dt} \quad (3.2.3)$$

$$= \langle l_T\rangle$$

Namely, the summation of mean path lengths $\langle l_{iT}\rangle = L_i(\mu_a)$ of the respective voxels over all the voxels against the time-resolved gate integration signal $I_T$ of the impulse response is equal to $\langle l_T\rangle$.

Next, integration of Eq. (3.2.2) with respect to $\mu_{ai}$ yields the following basic equation for the time-resolved gate integration signal $I_T$, because the scattering is independent on the absorption.

$$\ln I_T = \ln \int_{t_1}^{t_2} s(\mu_s, t)dt - \sum_{i=1}^{N}\int_0^{\mu_{ai}} L_i(\mu_a)d\mu_a \quad (3.2.4)$$

The first term on the right side is an integration constant, which is obtained by putting $\Sigma\mu_{ai}=0$ into Eq. (3.2.1). On this occasion, the first term on the right side indicates no relation with absorption, i.e., does the effects of scattering and boundary, and the second term on the right side indicates the attenuation $B_T$. By arranging the results so far, we obtain the following.

$$\frac{\partial \ln I_T}{\partial \mu_{ai}} = -\frac{\partial B_T}{\partial \mu_{ai}} = -\frac{\partial}{\partial \mu_{ai}} \sum_{i=1}^{N} \int_{0}^{\mu_{ai}} L_i(\mu_a) d\mu_a \quad (3.2.5)$$

A problem here is the dependency of $L_i(\mu_a)$ on the absorption coefficients of all voxels described above. Namely, existence of this dependency does not allow us to simplify this Eq. (3.2.5) further. This fact is significant and makes the optical CT image reconstruction algorithm complicated.

Incidentally, it is often the case in general that differences in absorption coefficients $\mu_{ai}$ between voxels, i.e., deviations thereof from the average absorption coefficient, are not so large. In this case, there is little influence of the absorption coefficient deviations of the other portions (or other voxels) on the mean path length $L_i(\mu_a)$ of the voxel i of interest. In other words, where the differences of absorption coefficient between voxels are small, the mean path length $L_i(\mu_a)$ of the voxel i of interest is determined roughly by an average of the absorption coefficients of all the voxels and a change of $L_i(\mu_a)$ dependent upon the deviations of the absorption coefficients of the other portions from the average absorption coefficient is negligibly small. Therefore, $L_i(\mu_a)$ can be regarded as a function of only the absorption coefficient $\mu_{ai}$ of the voxel i. In this case, the difference of $L_i(\mu_a)$, which corresponds to the difference between the absorption coefficient of the voxel i and the average absorption coefficient (the absorption coefficient deviation), can be described by linear approximation. Therefore, it is assumed hereinafter that $L_i(\mu_a)$ is a function of only the absorption coefficient $\mu_{ai}$ of the voxel i. Namely, where the mean path length $L_i(\mu_a)$ of the voxel i is of interest, it is assumed that the parameters other than the absorption coefficient $\mu_{ai}$ of the voxel i are constant (invariant). In the cases where absorption coefficients of two or more voxels vary simultaneously, a combined voxel of these two voxels is considered to be one new voxel. This is equivalent to the fact that "variations of absorption coefficients of plural voxels are unable to be quantified from one measurement value," and there is thus no theoretical contradiction.

With application of the above linear approximation, the following relation is obtained with definition of the attenuation $B_{iT}$ in the voxel i.

$$\frac{\partial \ln I_T}{\partial \mu_{ai}} = -\frac{\partial B_T}{\partial \mu_{ai}} \quad (3.2.6)$$

$$= -\frac{\partial}{\partial \mu_{ai}} \sum_{i=1}^{N} \int_{0}^{\mu_{ai}} L_i(\mu_a) d\mu_a$$

$$= -\frac{\partial}{\partial \mu_{ai}} \int_{0}^{\mu_{ai}} L_i(\mu_a) d\mu_a$$

$$= -\frac{\partial B_{iT}}{\partial \mu_{ai}} = -\langle l_{iT} \rangle = -L_i(\mu_{ai})$$

This equation indicates the MBL for the photon assemblage constituting the time-resolved gate integration signal $I_T$ of the inhomogeneous system. It is, however, noted that the aforementioned linear approximation was applied. When the integration range $[t_1, t_2]$ is $[0, \infty]$, the equation represents MBL for the ordinary time-resolved integration signal, i.e., for the stationary (CW) light.

Next, let us consider the weight functions $W_i$ for the time-resolved gate integration signal $I_T$. First, by modifying the attenuations $B_T$ and $B_{iT}$ of Eq. (3.2.4) and Eq. (3.2.6) using the mean value theorem, we obtain the following equations.

$$B_T = \sum_{i=1}^{N} \int_{0}^{\mu_{ai}} L_i(\mu_a) d\mu_a \quad (3.2.7.1)$$

$$= \sum_{i=1}^{N} [\mu_{ai} L_i(\mu_{x0})]$$

$$= \sum_{i=1}^{N} [\mu_{ai} W_{i0}]$$

$$B_{iT} = \int_{0}^{\mu_{ai}} L_i(\mu_a) d\mu_a = \mu_{ai} L_i(\mu_{x0}) = \mu_{ai} W_{i0} \quad (3.2.7.2)$$

However, $\mu_{x0}$ is an appropriate value to satisfy $0 \leq \mu_{x0} \leq \mu_{ai}$. From the definition of the weight function stated in section 2.4, it is thus seen that the weight function of the voxel i for the time-resolved gate integration signal $I_T$ is $W_{i0} = L_i(\mu_{x0})$. This weight function $W_{i0}$ is different from the mean path length $L_i(\mu_{ai}) = \langle l_{iT} \rangle$ of the voxel i for the time-resolved gate integration signal.

Eq. (3.2.5) needs to be used instead of Eq. (3.2.6) where the aforementioned dependency of $L_i(\mu_a)$ on the absorption of all the voxels is significant.

The above can also be applied to the ordinary time-resolved integration signal, i.e., the response to the stationary (CW) light by setting the integration range $[t_1, t_2]$ to $[0, \infty]$.

3.2.2 Absorption Dependency of Mean Path Length

The mean path length of each voxel is dependent on absorption of the voxel. The weight function is also dependent on the absorption of the voxel. In this section we analyze variations in the attenuation and mean path length occurring when the absorption coefficient $\mu_{ai}$ of the voxel i changes (by $\Delta \mu_{ai} = h$) to $(\mu_{ai} + h)$, and derive analytic equations to indicate their variation amounts. This will result in clarifying the difference between mean path length and weight function, which can raise a problem in image reconstruction of optical CT, and their absorption dependency.

First, the attenuation $B_{iT}$ of the voxel i indicated by Eq. (3.2.7.2) can be expressed as follows in the form of Taylor series with respect to $\mu_{ai}$.

$$B_{iT}(\mu_{ai} + h) = B_{iT}(\mu_{ai}) + \frac{h}{1!} B_{iT}^{(1)}(\mu_{ai}) + \frac{h^2}{2!} B_{iT}^{(2)}(\mu_{ai}) + \cdots \quad (3.2.8)$$

In this equation $B_{iT}^{(n)}(\mu_a)$ is the n-th order derivative of $B_{iT}(\mu_a)$ with respect to $\mu_a$. From the relation of Eq. (3.2.6), the following is obtained.

$$B_{iT}^{(1)}(\mu_{ai}) = \frac{\partial B_{iT}(\mu_{ai})}{\partial \mu_{ai}} = L_i(\mu_{ai}) \quad (3.2.9)$$

Therefore, $B_{iT}^{(2)}(\mu_{ai})$ is gained as follows using Eq. (3.2.2).

$$B_{iT}^{(2)}(\mu_{ai}) = L_i^{(1)}(\mu_{ai}) \quad (3.2.10)$$

$$= \frac{\partial}{\partial \mu_{ai}} \frac{\int_{0}^{\infty} l_i s(\mu_s, t) \exp\left(-\sum_{i=1}^{N} (\mu_{ai} l_i)\right) dt}{\int_{0}^{\infty} s(\mu_s, t) \exp\left(-\sum_{i=1}^{N} (\mu_{ai} l_i)\right) dt}$$

-continued $$= -\frac{\int_0^\infty (l_i - \langle l_{iT}\rangle)^2 s(\mu_s, t)\exp\left(-\sum_{i=1}^N (\mu_{ai}l_i)\right)dt}{\int_0^\infty s(\mu_s, t)\exp\left(-\sum_{i=1}^N (\mu_{ai}l_i)\right)dt}$$

$$= -\langle l_{iT}^2\rangle + \langle l_{iT}\rangle^2 = -\sigma_i^2(l_{iT})$$

Namely, $-B_{iT}^{(2)}(\mu_{ai}) = -L_i^{(1)}(\mu_{ai})$ indicates the variance around the average of $l_{iT}$. Therefore, the attenuation $B_{iT}(\mu_{ai})$ is given as follows.

$$B_{iT}(\mu_{ai} + h) = B_{iT}(\mu_{ai}) + hL_i(\mu_{ai}) - \frac{h^2}{2}\sigma_i^2(l_{iT}) + \cdots \quad (3.2.11)$$

A difference $\Delta B_{iT}$ between attenuations before and after change of the absorption coefficient from $\mu_{ai}$ to $(\mu_{ai}+h)$ is obtained as follows from Eq. (3.2.7.2).

$$\Delta B_{iT} = B_{iT}(\mu_{ai} + h) - B_{iT}(\mu_{ai}) \quad (3.2.12)$$

$$= \int_{\mu_{ai}}^{\mu_{ai}+h} L_i(\mu_a)d\mu_a = hL_i(\mu_x)$$

This $\mu_x$ is different from aforementioned $\mu_{x0}$ and is an appropriate value to satisfy the condition of $\min(\mu_{ai}, \mu_{ai}+h) \leq \mu_x \leq \max(\mu_{ai}, \mu_{ai}+h)$. This $L_i(\mu_x)$ is the weight function $W_i$ against the difference $\Delta B_{iT}$ of attenuation. By comparing Eq. (3.2.11) with Eq. (3.2.12), we can find the following relation.

$$W_i = L_i(\mu_x) = L_i(\mu_{ai}) - \frac{h}{2}\sigma_i^2(l_{iT}) + \cdots \quad (3.2.13)$$

On the other hand, the mean path length $L_i(\mu_{ai})$ can be written as follows in the form of Taylor series with respect to $\mu_{ai}$.

$$L_i(\mu_{ai} + h) = L_i(\mu_{ia}) + \frac{h}{1!}L_i^{(1)}(\mu_{ai}) + \frac{h^2}{2!}L_i^{(2)}(\mu_{ai}) + \cdots \quad (3.2.14)$$

In this equation $L_i^{(n)}(\mu_a)$ is the n-th order derivative of $L_i(\mu_a)$ with respect to $\mu_a$. Therefore, the following is gained from Eq. (3.2.13) and Eq. (3.2.14).

$$W_i = L_i(\mu_x) \approx L_i(\mu_{ai}) - \frac{h}{2}\sigma_i^2(l_{iT}) \quad (3.2.15)$$

$$= \frac{1}{2}[L_i(\mu_{ai} + h) + L_i(\mu_{ai})]$$

The approximation equation indicated by the right end side (the fourth formula) in Eq. (3.2.15) was already applied to quantitation of concentrations of absorptive constituents in the homogeneous scattering media by the inventors, and the validity thereof was verified by the inventors.

With the above in mind, where the absorption coefficient $\mu_{ai}$ of the voxel i changes to $(\mu_{ai}+h)$, a difference $\Delta I$ between time-resolved gate integration signals, $\ln I_T$, before and after the change is obtained as follows from Eq. (3.2.4).

$$\Delta I = \ln\frac{I(\mu_{ai})}{I(\mu_{ai} + h)} = \int_{\mu_{ai}}^{\mu_{ai}+h} L_i(\mu_a)d\mu_a \quad (3.2.16)$$

$$= hW_i = h\left(L_i(\mu_{ai}) - \frac{h}{2}\sigma_i^2(l_{iT})\right)$$

Namely, the absorption coefficient change $h = \Delta\mu_{ai}$ of the voxel i can be gained from the difference $\Delta I$ between time-resolved gate integration signals $\ln I_T$ of impulse response and the weight function $W_i$ under the absorption coefficient of $\mu_{ai}$. In this case, the weight function $W_i$ is a function of the mean path length $L_i(\mu_{ai}) = \langle l_{iT}\rangle$ and the variance $\sigma_i^2$ of a distribution of path lengths.

When the absorption coefficients $\mu_{ai}$ of some voxels i (voxels out of those 1 to N) change to $(\mu_{ai}+h_i)$, the difference $\Delta I$ between time-resolved gate integration signals $\ln I_T$ before and after the change is gained as follows from Eq. (3.2.4).

$$\Delta I = \sum_{i=1}^N \int_{\mu_{ai}}^{\mu_{ai}+h_i} L_i(\mu_a)d\mu_a = \sum_{i=1}^N [h_i W_i] \quad (3.2.17)$$

$$\approx \sum_{i=1}^N \left[h_i\left(L_i(\mu_{ai}) - \frac{h_i}{2}\sigma_i^2(l_{iT})\right)\right]$$

Namely, the absorption coefficient changes $h_i = \Delta\mu_{ai}$ of the plural voxels i (i=1 to N) can be obtained from the difference $\Delta I$ between time-resolved gate integration signals $\ln I_T$ of impulse response and the weight function $W_i$ under the absorption coefficient of $\mu_{ai}$. In this case, it is necessary, however, to solve N simultaneous equations, and thus N independent measurements $\Delta I$ are necessary. The aforementioned weight function $W_i$ is a function of the mean path length $L_i(\mu_{ai}) = \langle l_{iT}\rangle$ and the variance $\sigma_i^2$ of a distribution of path lengths.

In the above case, the accuracy is improved when the absorption coefficients $\mu_{ai}$ are selected so as to be equal or close to the average absorption coefficient of the medium to be measured. Namely, the problem of dependency of $L_i(\mu_a)$ on the absorption of all voxels as stated previously is relaxed greatly.

If the deviation of the absorption coefficient $\mu_a$ of each voxel from the average absorption coefficient is extremely large and if the dependency of $L_i(\mu_a)$ on the absorption coefficient deviations of the other voxels poses a problem, iterative computations to return to Eq. (3.2.5) and execute recomputation will become necessary.

The above can be applied to the ordinary time-resolved integration signal, i.e., to the response to the stationary (CW) light by setting the integration range $[t_1, t_2]$ to $[0, \infty]$.

3.2.3 Application to Average Value Method

The optical CT is an approach to measurement of concentration distribution of absorptive constituents in the inhomogeneous media. In this case, problems are made complex by the aforementioned two types of absorption dependency of the mean path length, i.e., the dependency of $L_i(\mu_a)$ on absorption of all voxels and the dependency of $L_i(\mu_a)$ on absorption of the voxel i itself. The inventors developed the Average Value Method (hereinafter referred to as "AVM") as a method for reducing errors based on these absorption dependencies. This AVM is a method of estimating or measuring an approximate average absorption coefficient for an inhomogeneous medium to be measured and quantitating a deviation of the absorption coefficient in each part of the medium, with respect to this average value. In this case, the average absorption coefficient estimated or measured above does not have to be equal to a true value. This method greatly relaxes the problem of the absorption coefficient dependency of the mean path length and improves the accuracy of reconstructed optical CT image more and more as the average absorption coefficient estimated or measured above becomes closer and closer to the true value.

Now let us assume an imaginary medium having the absorption coefficient Ftav close to the average absorption coefficient of the medium to be measured $(\mu_a = \mu_{av})$. Then the absorption coefficients of the inhomogeneous medium as the measured object are given by $\mu_{ai}=\mu_{av}+\Delta\mu_{ai}$ (i=1 to N). When the time-resolved gate integration measurement is assumed, the relation between measurements $I(\mu_{aV})$ of the imaginary medium and measurements I $(\mu_{ai}=\mu_{av}+\Delta\mu_{ai})$ (i=1 to N) of the actual medium is given as follows from Eq. (3.2.4) and Eq. (3.2.15) or from Eq. (3.2.17).

$$\Delta I = \ln\frac{I_T(\mu_{av})}{I_T(\mu_{av}+\Delta\mu_{ai})} = \sum_{i=1}^{N}\int_{\mu_{av}}^{\mu_{av}+\Delta\mu_{ai}}L_i(\mu_a)d\mu_a \quad (3.2.18)$$

$$= \sum_{i=1}^{N}[\Delta\mu_{ai}W_i]$$

$$= \sum_{i=1}^{N}\left[\Delta\mu_{ai}\left(L_i(\mu_{av})-\frac{1}{2}\Delta\mu_{ai}\sigma_{iv}^2(l_{iT})\right)\right]$$

Namely, the absorption coefficient deviations $\Delta\mu_{ai}$ of plural voxels i (i=1 to N) can be gained from the difference $\Delta I$ between time-resolved gate integration signals $\ln I_T$ of impulse responses to the imaginary medium and the actual medium, and the weight function $W_i$ under the absorption coefficient of $\mu_{av}$. However, it is necessary to solve N simultaneous equations in this case, and thus N independent measurement values $\Delta I$ are necessary. The weight function $W_i$ is a function of the mean path length $L_i(\mu_{av})=<l_{iT}>$ and the variance $\sigma_{iv}^2$ thereof under the absorption coefficient of $\mu_{av}$. The mean path length and variance of the voxel i of the medium (imaginary medium) demonstrating the uniform absorption as described above can be computed by Monte Carlo simulations and the like.

Aforementioned Eq. (3.2.18) can be expressed in the form of a matrix representation as follows.

$$\begin{bmatrix}\Delta I_1\\\Delta I_2\\\vdots\\\Delta I_N\end{bmatrix}=\begin{bmatrix}W_{11}&W_{12}&\cdots&W_{1N}\\\vdots&\ddots&&\vdots\\W_{N1}&&\cdots&W_{NN}\end{bmatrix}\begin{bmatrix}\Delta\mu_{a1}\\\Delta\mu_{a2}\\\vdots\\\Delta\mu_{aN}\end{bmatrix} \quad (3.2.19)$$

The weight functions $W_i$ herein are given as follows.

$$W_i = L_i(\mu_x) = L_i(\mu_{av})-\frac{\Delta\mu_{ai}}{2}\sigma_{iv}^2(l_{iT}) \quad (3.2.20)$$

$$=\frac{1}{2}[L_i(\mu_{av}+\Delta\mu_{ai})+L_i(\mu_{av})]$$

3.3 Response in Frequency Domain of Inhomogeneous System

The response in the frequency domain is gained as follows by the Fourier transformation of the impulse response h(t) given by aforementioned Eq. (3.1.8).

$$H(\omega)=\int_0^\infty h(t)\exp(-j\omega t)dt \quad (3.3.1.1)$$

$$=\int_0^\infty s(\mu_s,t)\exp(-b)\exp(-j\omega t)dt$$

$$=R(b,\omega)+jX(b,\omega)$$

$$=A(b,\omega)\exp[-j\phi(b,\omega)]$$

$$b=\sum_{i=1}^{N}(\mu_{ai}ct_i) \quad (3.3.1.2)$$

In the above equation, R, X, A, and $\phi$ are defined as follows.

$$R=\int_0^\infty s(\mu_s,t)\exp\left[-\sum_{i=1}^{N}(\mu_{ai}ct_i)\right]\cos\omega t\,dt \quad (3.3.2.1)$$

$$X=-\int_0^\infty s(\mu_s,t)\exp\left[-\sum_{i=1}^{N}(\mu_{ai}ct_i)\right]\sin\omega t\,dt \quad (3.3.2.2)$$

$$A=(R^2+X^2)^{\frac{1}{2}} \quad (3.3.2.3)$$

$$\phi=-\tan^{-1}\frac{X}{R} \quad (3.3.2.4)$$

Namely, R and X are the real part and the imaginary part, respectively, and A and $\phi$ are the amplitude and phase dalay, respectively. These can be measured readily by a lock-in amplifier or the like.

Then we can obtain the following relations, as detailed hereinafter.

$$\frac{\partial R}{\partial\mu_{ai}}=c\frac{\partial X_i}{\partial\omega} \quad (3.3.3.1)$$

$$\frac{\partial X}{\partial\mu_{ai}}=-c\frac{\partial R_i}{\partial\omega} \quad (3.3.3.2)$$

$$\frac{\partial\ln A}{\partial\mu_{ai}}=-c\frac{\partial\phi_i}{\partial\omega} \quad (3.3.3.3)$$

$$\frac{\partial\phi}{\partial\mu_{ai}}=c\frac{\partial\ln A_i}{\partial\omega} \quad (3.3.3.4)$$

In these relations, the parameters provided with the subscript i on the right sides of the respective equations represent quantities in the voxel i, which correspond to the mean path length discussed in the previous section. Here the following relations are also defined, as detailed hereinafter.

$$\frac{\partial R_i}{\partial\omega}\equiv-\int_0^\infty t_i s(\mu_s,t)\exp\left[-\sum_{i=1}^{N}(\mu_{ai}ct_i)\right]\sin\omega t\,dt \quad (3.3.4.1)$$

$$\frac{\partial X_i}{\partial\omega}\equiv-\int_0^\infty t_i s(\mu_s,t)\exp\left[-\sum_{i=1}^{N}(\mu_{ai}ct_i)\right]\cos\omega t\,dt \quad (3.3.4.2)$$

$$\frac{\partial\ln A_i}{\partial\omega}\equiv\frac{1}{A^2}\left(R\frac{\partial R_i}{\partial\omega}+X\frac{\partial X_i}{\partial\omega}\right) \quad (3.3.4.3)$$

$$\frac{\partial\phi_i}{\partial\omega}\equiv-\frac{1}{A^2}\left(R\frac{\partial X_i}{\partial\omega}-X\frac{\partial R_i}{\partial\omega}\right) \quad (3.3.4.4)$$

In the above, the following relations hold.

$$\frac{\partial\ln A}{\partial\omega}=\sum_{i=1}^{N}\frac{\partial\ln A_i}{\partial\omega} \quad (3.3.5.1)$$

$$\frac{\partial\phi}{\partial\omega}=\sum_{i=1}^{N}\frac{\partial\phi_i}{\partial\omega} \quad (3.3.5.2)$$

Therefore, the following relations are gained from the relations of Eq. (3.3.3.1) to Eq. (3.3.3.4) in the similar manner to the derivation of aforementioned Eq. (3.2.4).

$$R = R\left(\sum_{i=1}^{N}(\mu_{ai}t_i)=0\right) + c\sum_{i=1}^{N}\int_{0}^{\mu_{ai}}\frac{\partial X_i}{\partial \omega}d\mu_a \quad (3.3.6.1)$$

$$X = X\left(\sum_{i=1}^{N}(\mu_{ai}t_i)=0\right) - c\sum_{i=1}^{N}\int_{0}^{\mu_{ai}}\frac{\partial R_i}{\partial \omega}d\mu_a \quad (3.3.6.2)$$

$$\ln A = \ln A\left(\sum_{i=1}^{N}(\mu_{ai}t_i)=0\right) - c\sum_{i=1}^{N}\int_{0}^{\mu_{ai}}\frac{\partial \phi_i}{\partial \omega}d\mu_a \quad (3.3.6.3)$$

$$\phi = \phi\left(\sum_{i=1}^{N}(\mu_{ai}t_i)=0\right) + c\sum_{i=1}^{N}\int_{0}^{\mu_{ai}}\frac{\partial \ln A_i}{\partial \omega}d\mu_a \quad (3.3.6.4)$$

Each of the first terms in the right sides is an integration constant and is obtained by substituting $\Sigma\mu_{ai}=0$ into the corresponding parameter in the left side.

Since Eq. (3.3.6.1) to Eq. (3.3.6.4) above are similar to the equations for time-resolved gate integration signal described in the previous section, these equations can be modified in a fashion similar to those in the previous section. The case of Eq. (3.3.6.3) will be discussed below as an example. First, let us consider the weight functions for the response in the frequency domain, as in the previous section. First, the attenuation term of Eq. (3.3.6.3) (the second term in the right side) can be written as follows by use of the mean value theorem.

$$B_f = c\sum_{i=1}^{N}\int_{0}^{\mu_{ai}}\frac{\partial \phi_i}{\partial \omega}d\mu_a = c\sum_{i=1}^{N}\left(\left[\mu_{ai}\frac{\partial \phi_i}{\partial \omega}\right]\bigg|_{\mu_x}\right) \quad (3.3.7.1)$$

$$\left(B_{if} = \int_{0}^{\mu_{ai}}c\frac{\partial \phi_i}{\partial \omega}d\mu_a = \mu_{ai}c\frac{\partial \phi_i}{\partial \omega}\bigg|_{\mu_x}\right) \quad (3.3.7.2)$$

In these equations, $$c\frac{\partial \phi_i}{\partial \omega}\bigg|_{\mu_x} \quad (3.3.7.3)$$

is the weight function (c×group delay) of the voxel i for detected light, i.e., the weight function of the response in the frequency domain. It is, however, noted that $\mu_x$ is an appropriate value to satisfy $0 \leq \mu_x \leq \mu_{ai}$. This weight function (3.3.7.3) corresponds to the weight function $W_i(\mu_x)=L_i(\mu_x)$ stated in the previous section and takes a value different from the value indicated by (3.3.7.5) below, which is c times an average group delay of the voxel i indicated by (3.3.7.4) below.

$$\frac{\partial \phi_i}{\partial \omega} \quad (3.3.7.4)$$

$$c\frac{\partial \phi_i}{\partial \omega} \quad (3.3.7.5)$$

Further, absorption coefficient dependencies of the attenuation $B_{if}$ and average group delay (3.3.7.4) of the voxel i are similar to those of the attenuation $B_{iT}$ and mean path length $L_i(\mu_x)$ stated in the previous section. Namely, as to the absorption dependency of the group delay (3.3.7.4), it is derived as follows from Eq. (3.3.3.4) and Eq. (3.3.5.2).

$$c\frac{\partial^2 \ln A_i}{\partial \omega^2} = \frac{\partial}{\partial \omega}\frac{\partial \phi}{\partial \mu_{ai}} = \frac{\partial \phi}{\partial \mu_{ai}}\frac{\partial \phi}{\partial \omega} \quad (3.3.8)$$

$$= \frac{\partial \phi}{\partial \mu_{ai}}\sum_{i=1}^{N}\frac{\partial \phi_i}{\partial \omega} = \frac{\partial}{\partial \mu_{ai}}\frac{\partial \phi_i}{\partial \omega}$$

It is, however, noted that the following is assumed between different voxels (where $i \neq j$).

$$\frac{\partial}{\partial \mu_{ai}}\frac{\partial \phi_j}{\partial \omega} = 0 \quad (i \neq j) \quad (3.3.9)$$

Namely, the average group delay (3.3.7.4) is assumed to be independent of the group delays of the voxels other than the voxel i, i.e., independent of the following.

$$\frac{\partial \phi_j}{\partial \omega} \quad (j \neq i)$$

These are similar to the assumption in the previous section. It is noted that:

$$\frac{\partial^2 \ln A}{\partial \omega^2}$$

in the above equation can be measured using three types of modulation frequencies.

From the above, we can obtain the following equations in the same manner to the aforementioned discussion (in section 3.2.3).

$$c\frac{\partial \phi_i}{\partial \omega}\bigg|_{\mu_x} \approx c\frac{\partial \phi_i}{\partial \omega}\bigg|_{\mu_{ai}} - \frac{h}{2}\sigma_f^2 = \frac{c}{2}\left[\frac{\partial \phi_i}{\partial \omega}\bigg|_{\mu_{ai}+h} + \frac{\partial \phi_i}{\partial \omega}\bigg|_{\mu_{ai}}\right] \quad (3.3.10)$$

$$\sigma_f^2 = c^2\frac{\partial}{\partial \mu_{ai}}\frac{\partial \phi_i}{\partial \omega} = c^2\partial^2 \ln\frac{A_i}{\partial \omega^2} \quad (3.3.11)$$

On this occasion, the average group delay and variance of the voxel i in the medium (imaginary medium) demonstrating uniform absorption ($\mu_{ai}=\mu_{av}$) can be computed by the Monte Carlo simulations or the like. Therefore, where $\mu_{ai}$ is known, the average group delay under the absorption coefficient of $\mu_x$:

$$\frac{\partial \phi_i}{\partial \omega}\bigg|_{\mu_x}$$

can be computed.

[Derivation of Eq. (3.3.3.1) to Eq. (3.3.3.4)]

First, taking $t=\Sigma t_i$ into consideration, the following equations are yielded from Eq. (3.3.2.1) and Eq. (3.3.2.2).

$$\frac{\partial R}{\partial \omega} = -\int_{0}^{\infty}ts(\mu_s,t)\exp\left[-\sum_{i=1}^{N}(\mu_{ai}ct_i)\right]\sin\omega t dt \quad (B.1.1)$$

$$= -\sum_{i=1}^{N}\int_{0}^{\infty}t_i s(\mu_s,t)\exp\left[-\sum_{i=1}^{N}(\mu_{ai}ct_i)\right]\sin\omega t dt$$

-continued $$\frac{\partial X}{\partial \omega} = -\int_0^\infty ts(\mu_s, t) \exp\left[-\sum_{i=1}^N (\mu_{ai} ct_i)\right] \cos\omega t \, dt \quad \text{(B.1.2)}$$

$$= -\sum_{i=1}^N \int_0^\infty t_i s(\mu_s, t) \exp\left[-\sum_{i=1}^N (\mu_{ai} ct_i)\right] \cos\omega t \, dt$$

Then let us define the following.

$$\frac{\partial R_i}{\partial \omega} = -\int_0^\infty t_i s(\mu_s, t) \exp\left[-\sum_{i=1}^N (\mu_{ai} ct_i)\right] \sin\omega t \, dt \quad \text{(B.2.1)}$$

$$\frac{\partial X_i}{\partial \omega} = -\int_0^\infty t_i s(\mu_s, t) \exp\left[-\sum_{i=1}^N (\mu_{ai} ct_i)\right] \cos\omega t \, dt \quad \text{(B.2.2)}$$

In this case, the following relations hold.

$$\frac{\partial R}{\partial \omega} = \sum_{i=1}^N \frac{\partial R_i}{\partial \omega} \quad \text{(B.3.1)}$$

$$\frac{\partial X}{\partial \omega} = \sum_{i=1}^N \frac{\partial X_i}{\partial \omega} \quad \text{(B.3.2)}$$

The following equations are also gained from Eq. (3.3.2.1) and Eq. (3.3.2.2).

$$\frac{\partial R}{\partial \mu_{ai}} = -c \int_0^\infty t_i s(\mu_s, t) \exp\left[-\sum_{i=1}^N (\mu_{ai} ct_i)\right] \cos\omega t \, dt \quad \text{(B.4.1)}$$

$$\frac{\partial X}{\partial \mu_{ai}} = c \int_0^\infty t_i s(\mu_s, t) \exp\left[-\sum_{i=1}^N (\mu_{ai} ct_i)\right] \sin\omega t \, dt \quad \text{(B.4.2)}$$

From the above, the following equations are yielded.

$$\frac{\partial R}{\partial \mu_{ai}} = c \frac{\partial X_i}{\partial \omega} \quad (3.3.3.1)$$

$$\frac{\partial X}{\partial \mu_{ai}} = -c \frac{\partial R_i}{\partial \omega} \quad (3.3.3.2)$$

Further, we can obtain the following from Eq. (3.3.2.3) and the above equations.

$$\frac{\partial \ln A}{\partial \mu_{ai}} = \frac{1}{A} \frac{\partial A}{\partial \mu_{ai}} \quad \text{(B.5)}$$

$$= \frac{1}{A^2}\left(R\frac{\partial R}{\partial \mu_{ai}} + X\frac{\partial X}{\partial \mu_{ai}}\right)$$

$$= \frac{c}{A^2}\left(R\frac{\partial X_i}{\partial \omega} - X\frac{\partial R_i}{\partial \omega}\right) = -c\frac{\partial \phi_i}{\partial \omega}$$

It is, however, noted that the following definition was employed.

$$\frac{\partial \phi_i}{\partial \omega} \equiv -\frac{1}{A^2}\left(R\frac{\partial X_i}{\partial \omega} - X\frac{\partial R_i}{\partial \omega}\right) \quad \text{(B.6)}$$

In this case, the following is obtained by putting Eq. (B.3.1) and Eq. (B.3.2) into the above equation.

$$\sum_{i=1}^N \frac{\partial \phi_i}{\partial \omega} = -\frac{1}{A^2}\sum_{i=1}^N \left(R\frac{\partial X_i}{\partial \omega} - X\frac{\partial R_i}{\partial \omega}\right) \quad \text{(B.7)}$$

$$= -\frac{1}{A^2}\left(R\frac{\partial X}{\partial \omega} - X\frac{\partial R}{\partial \omega}\right)$$

$$= -\cos^2\phi \frac{\partial}{\partial \omega}\frac{X}{R}$$

$$= \cos^2\phi \frac{\partial}{\partial \omega}\tan\phi = \frac{\partial \phi}{\partial \omega}$$

This yields the following.

$$\frac{\partial \phi}{\partial \omega} = \sum_{i=1}^N \frac{\partial \phi_i}{\partial \omega} \quad \text{(B.8)}$$

From the above, we obtain Eq. (3.3.3.3).

The following is also derived similarly from Eq. (3.3.2.4), Eq. (3.3.3.1), and Eq. (3.3.3.2).

$$\frac{\partial \phi}{\partial \mu_{ai}} = -\frac{1}{A^2}\left(R\frac{\partial X}{\partial \mu_{ai}} - X\frac{\partial R}{\partial \mu_{ai}}\right) \quad \text{(B.9)}$$

$$= \frac{c}{A^2}\left(R\frac{\partial R_i}{\partial \omega} + X\frac{\partial X_i}{\partial \omega}\right) = c\frac{\partial \ln A_i}{\partial \omega}$$

It is, however, noted that the following definition was employed.

$$\frac{\partial \ln A_i}{\partial \omega} \equiv \frac{1}{A^2}\left(R\frac{\partial R_i}{\partial \omega} + X\frac{\partial X_i}{\partial \omega}\right) \quad \text{(B.10)}$$

Therefore, we obtain the following.

$$\frac{\partial \phi}{\partial \mu_{ai}} = c\frac{\partial \ln A_i}{\partial \omega} \quad (3.3.3.4)$$

Under the above circumstances, the following relation holds.

$$\sum_{i=1}^N \frac{\partial \ln A_i}{\partial \omega} = \frac{1}{A^2}\sum_{i=1}^N \left(R\frac{\partial R_i}{\partial \omega} + X\frac{\partial X_i}{\partial \omega}\right) \quad \text{(B.11)}$$

$$= \frac{1}{A^2}\left(R\sum_{i=1}^N \frac{\partial R_i}{\partial \omega} + X\sum_{i=1}^N \frac{\partial X_i}{\partial \omega}\right)$$

$$= \frac{1}{A^2}\left(R\frac{\partial R}{\partial \omega} + X\frac{\partial X}{\partial \omega}\right) = \frac{\partial \ln A}{\partial \omega}$$

Therefore, the following relation holds.

$$\frac{\partial \ln A}{\partial \omega} = \sum_{i=1}^N \frac{\partial \ln A_i}{\partial \omega} \quad \text{(B.12)}$$

4. General Expression Concerning Inhomogeneous Systems

As apparent from the description up to the previous section, the MBL for the inhomogeneous systems is expressed effectively in the differential form. Namely, Eq. (3.1.6) to indicate the attenuation $B_h$ of the impulse response h(t) for the inhomogeneous system, Eq. (3.2.6) to indicate the attenuation $B_T$ of the time-resolved gate integration signal $I_T(\mu_s, \mu_a)$ of the impulse response, Eq. (3.3.3.3) to indicate the attenuation $B_f$ of the amplitude A detected in measurement in the frequency domain, etc. are expressed in the differential form and those equations are similar.

Letting Y be these responses (the predetermined parameter of detected light), B be the attenuation, and $Z_i$ be the mean path length of each voxel, the above various responses can be expressed together in the general equation below.

$$\frac{\partial \ln Y}{\partial \mu_{ai}} = -\frac{\partial B}{\partial \mu_{ai}} = -Z_i(\mu_{ai}) \tag{4.1}$$

In the above, where a response of interest is comprised of a plurality of photons of different path lengths, the mean path length Z is a function of $\mu_{ai}$. if a response of interst is comprised of photons having an equal path length l, the mean path length is given by $Z_i = l_i$ determined by the photon path distribution ($\mu_a = 0$) and this $l_i$ is independent of $\mu_{ai}$. As apparent from the above, Eq. (4.1) represents the general expression of MBL for the inhomogeneous systems. Namely, this Eq. (4.1) indicates that the attenuation in the inhomogeneous media is determined by only the absorption coefficient and the mean path length of each voxel. Therefore, the MBL for the inhomogeneous systems may be considered to be the description of this fact.

Setting $S(\mu_s)$ as a response under $\mu_a = 0$, we obtain the following equations from above Eq. (4.1).

$$\ln Y = \ln S(\mu_s) - B \tag{4.2}$$
$$= \ln S(\mu_s) - \sum_{i=1}^{N} \int_0^{\mu_{ai}} Z_i(\mu_a) d\mu_a$$
$$= \ln S(\mu_s) - \sum_{i=1}^{N} (\mu_{ai} W_i)$$

$$Y = S(\mu_s)\exp(-B) \tag{4.3}$$
$$= S(\mu_s)\exp\left[-\sum_{i=1}^{N} \int_0^{\mu_{ai}} Z_i(\mu_a) d\mu_a\right]$$
$$= S(\mu_s)\exp\left[-\sum_{i=1}^{N} (\mu_{ai} W_i)\right]$$

Here $W_i$ is the weight function of each voxel.

Now let us explain the relation to the optical CT image reconstruction by AVM for quantitating the absorption coefficient distribution of each part of a medium, based on a value close to the average absorption coefficient of the inhomogeneous medium. In this case, it is assumed that a value $\mu_{av}$ close to the average absorption coefficient of the inhomogeneous medium is known and the absorption coefficient of the voxel i is $\mu_{av} + \Delta\mu_{ai}$. Just as in section 3.2.3, assuming that $Z_i(\mu_{ai})$ is a function of only $\mu_{ai}$ within the range of the deviation $\Delta\mu_{ai}$ of absorption coefficient, we can obtain the following relation in a similar fashion to Eq. (3.2.18).

$$\Delta Y = \ln \frac{Y(\mu_{av})}{Y(\mu_{av} + \Delta\mu_{ai})} = \sum_{i=1}^{N} \int_{\mu_{av}}^{\mu_{av}+\Delta\mu_{ai}} Z_i(\mu_a) d\mu_a \tag{4.4}$$
$$= \sum_{i=1}^{N} [\Delta\mu_{ai} W_i] = \sum_{i=1}^{N} \left[\Delta\mu_{ai}\left(Z_i(\mu_{av}) - \frac{1}{2}\Delta\mu_{ai}\sigma_{iv}^2\right)\right]$$

Here $\sigma_{iv}^2$ indicates the variance. A matrix representation of Eq. (4.4) is as follows.

$$\begin{bmatrix} \Delta Y_1 \\ \Delta Y_2 \\ \vdots \\ \Delta Y_N \end{bmatrix} = \begin{bmatrix} W_{11} & W_{12} & \cdots & W_{1N} \\ \vdots & \ddots & & \vdots \\ W_{N1} & & \cdots & W_{NN} \end{bmatrix} \begin{bmatrix} \Delta\mu_{a1} \\ \Delta\mu_{a2} \\ \vdots \\ \Delta\mu_{aN} \end{bmatrix} \tag{4.5}$$

The weight functions $W_i$ herein are expressed as follows.

$$W_i = Z_i(\mu_x) = Z_i(\mu_{av}) - \frac{\Delta\mu_{ai}}{2}\sigma_{iv}^2 \tag{4.6}$$

The mean path length and variance of the voxel i of the medium (imaginary medium) demonstrating the uniform absorption can be computed by Monte Carlo simulations or the like. When the dependency of $Z_i(\mu_{ai})$ on the absorption of all voxels as discussed previously poses a problem, it is necessary to perform such iterative computations as to return to Eq. (4.7) below and execute recalculation.

$$\frac{\partial \ln Y}{\partial \mu_{ai}} = -\frac{\partial B}{\partial \mu_{ai}} = -\frac{\partial}{\partial \mu_{ai}}\sum_{i=1}^{N} \int_0^{\mu_{ai}} Z_i(\mu_a) d\mu_a \tag{4.7}$$

(First Embodiment)

Figure 2:
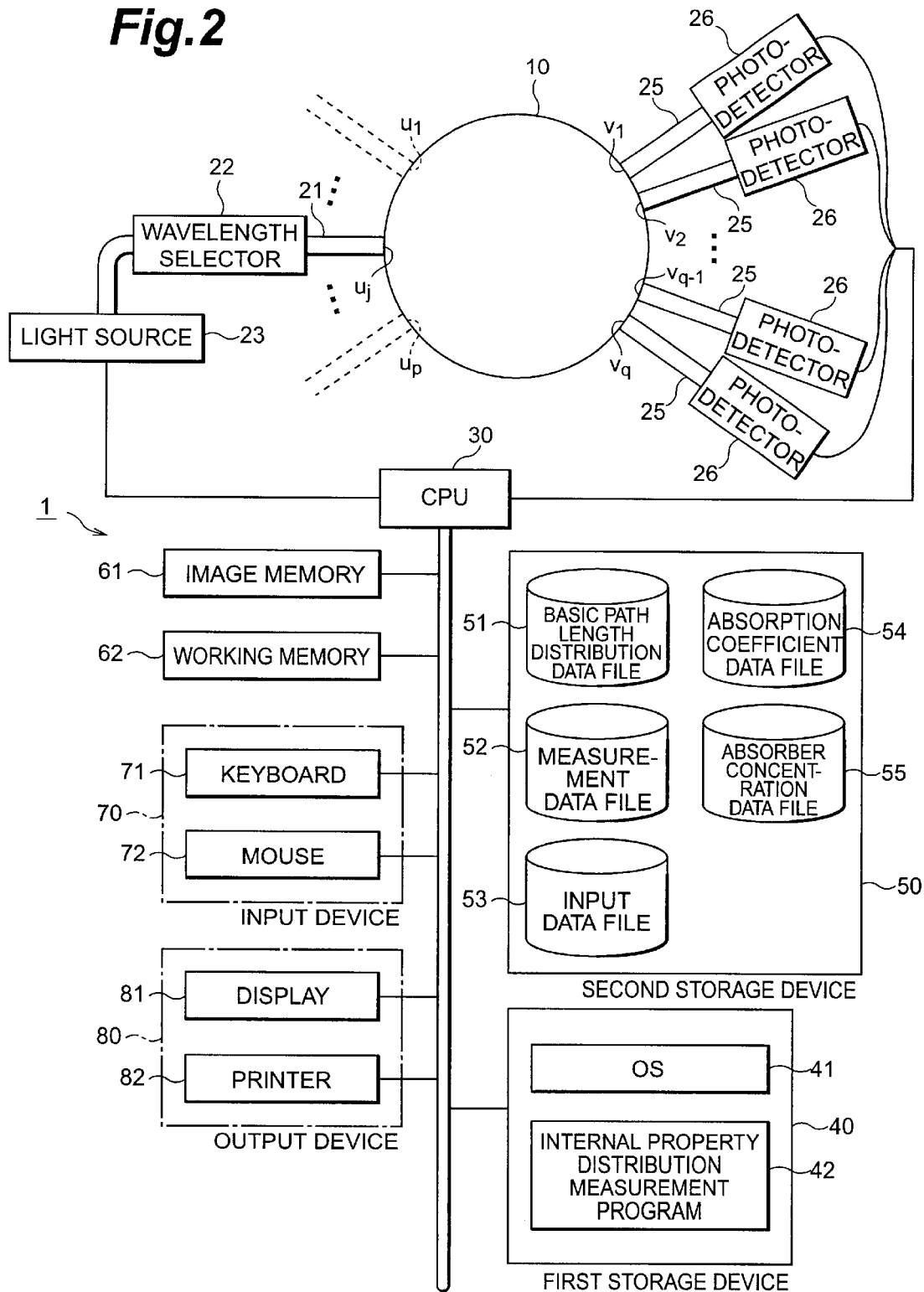
FIG. 2 is a schematic diagram to show an embodiment of the apparatus for measuring an internal property distribution of a scattering medium according to the present invention.

The first embodiment, which is a preferred embodiment of the present invention, will be described with reference to FIG. 2 to FIG. 6. FIG. 2 shows an internal property distribution measuring system (optical CT image measuring device) 1 for measuring a concentration distribution of an absorptive constituent distributed inside a medium 10 to be measured, which is a scattering medium. First, let us describe the structure of the internal property distribution measuring system 1.

The system illustrated in FIG. 2 is provided with a light injection fiber 21 and the tip of the light injection fiber 21 is arranged to be movable to different positions $u_j$ $(j=1$ to p) on the surface of the measured medium 10. A light source 23 is optically connected through a wavelength selector 22 to the light injection fiber 21 and rays emitted from the light source 23 are subjected to wavelength selection in the wavelength selector 22 and then successively injected through the light injection fiber 21 from the different positions $u_j$ (j=1 to p) into the measured medium 10. The light source 23 can be one selected from various sources including light emitting diodes, laser diodes, He-Ne lasers, and so on. The light source 23 may be one of those generating pulsed rays, rectangular rays, or modulated rays thereof. The light source 23 used in the present embodiment may be one generating rays of a single wavelength or one capable of generating rays of two or more wavelengths.

The system illustrated in FIG. 2 is also provided with a plurality of light detection fibers 25 and tips of the respective light detection fibers 25 are located at a plurality of positions $v_k$ (k=1 to q) on the surface of the measured medium 10. Each of the light detection fibers 25 is optically connected to a photodetector 26 and rays traveling through while being scattered in the measured medium 10 are guided through the light detection fibers 25 to the photodetectors 26. The photodetectors 26 convert their respective, received light signals into detection signals (electrical signals) and amplify the detection signals to output their respectively corresponding detection signals. The photodetectors 26 can be selected from all types of photodetectors including photomultiplier tubes, phototubes, photodiodes, avalanche photodiodes, PIN photodiodes, and so on. The point necessary for the selection of the photodetectors 26 is that the photodetectors have spectral sensitivity characteristics enough to detect light of the wavelength of the measurement light (measurement rays) used. When light signals are weak, it is preferable to use the photodetectors with high sensitivity or with high gain.

It is desirable to employ light-absorbing or intercepting structure at the other places than the light injection surface via the light injection fiber 21 and than the light detection surface via the light detection fibers 25 on the surface of the measured medium 10. A wavelength selecting filter (not illustrated) may also be properly placed between each pair of photodetector 26 and light detection fiber 25 if the rays having diffused and propagated inside the measured medium 10 include rays of plural wavelengths.

A CPU (control and processing unit) 30 is electrically connected to the light source 23 and to the photodetectors 26. The CPU 30 controls timing of light detection in synchronism with light injection, and other operations, and the detection signals outputted from the photodetectors 26 are guided to the CPU 30. In the case of the measurement using the measurement rays having a plurality of wavelengths, the CPU 30 also controls the wavelengths of injected rays. Specific control techniques include a technique of injecting and using rays of the different wavelengths in time-shared manner, and a technique of using light simultaneously including the rays of the different wavelengths. Specific wavelength selecting means include a beam switch using a mirror, a wavelength switch using a filter, a light switch using an optical switch, and so on.

The above light injection fiber 21, wavelength selector 22, light source 23, and CPU 30 constitute the light injection means according to the present invention, and the above light detection fibers 25, photodetectors 26, and CPU 30 constitute the light detection means according to the present invention.

The internal property distribution measuring system 1 illustrated in FIG. 2 further has a first storage device 40 storing an operating system (OS) 41 and an internal property distribution measurement program 42 detailed hereinafter, a second memory device 50 storing various files, an image memory 61 for storing optical CT image data to indicate the internal property distribution obtained, a working memory 62 for temporarily saving working data, an input device 70 equipped with a keyboard 71 and a mouse 72 for entry of data, and an output device 80 equipped with a display 81 and a printer 82 for output of resultant data, which are also controlled by the CPU 30 electrically connected thereto. The above storage devices and memories may be an internal memory (hard disk) of a computer or a flexible disk.

The second storage device 50 includes a basic path length distribution data file 51, a measurement data file 52, an input data file 53, an absorption coefficient data file 54, and an absorber concentration data file 55.

Among them, the basic path length distribution data file 51 stores a basic path length distribution preliminarily prepared (which is a common path length distribution as a basis for the operation of various weight functions used in various measurements). This basic path length distribution can be computed by making use of the known techniques, for example, by using the Monte Carlo simulations and the photon diffusion equation, which are described, for example, in the following references: (17) J. Haselgrove, J. Leigh, C. Yee, N-G, Wang, M. Maris and B. Chance: Proc. SPIE, Vol. 1431, 30–41 (1991); (18) J. C. Schotland, J. C. Haselgrove and J. S. Leigh: Appl. Opt. 32, 448–453 (1993); (19) Y. Tsuchiya, K. Ohta and T. Urakami: Jpn. J. Appl. Opt. 34, 2495–2501 (1995); (20) S. R. Arrige: Appl. Opt. 34, 7395–7409 (1995).

Preset measurement conditions and known values are entered through the input device 70 and such input data is stored in the input data file 53. Such input data includes the arbitrarily preset number, shape, and size of voxels (volume elements), the shape of the measured medium, the light injection positions, the light detection positions, the scattering coefficient, the average absorption coefficient, the wavelength of rays used in measurement, the type of measurement (time-resolved integration measurement, time-resolved gate integration measurement, phase modulation measurement, etc.), an extinction ratio of an absorber as a measured object at a predetermined wavelength, and so on.

Further, the measurement data file 52 stores measurement values of the predetermined parameter obtained, based on the detection signals from the photodetectors 26, in an execution process of the internal property distribution measurement program 42, in correspondence to combinations of the light injection positions with light detection positions. The absorption coefficient data file 54 and the absorber concentration data file 55 store the absorption coefficient data and absorber concentration data obtained by execution of the internal property distribution measurement program 42.

The above CPU 30, first storage device 40, and second storage device 50 constitute the measurement acquisition means, the reference value setting means, the estimate computation means, the weight function operation means, the absorption coefficient deviation computation means, the absorption coefficient absolute value computation means, and the concentration computation means according to the present invention, and the above output device 80 does the image display means. These various means according to the present invention will be detailed below, based on a flowchart of an embodiment of the method of the present invention illustrated in FIG. 3 and FIG. 4 (which is a flowchart to indicate processing of the internal property distribution measurement program 42 illustrated in FIG. 2).

Figure 3:
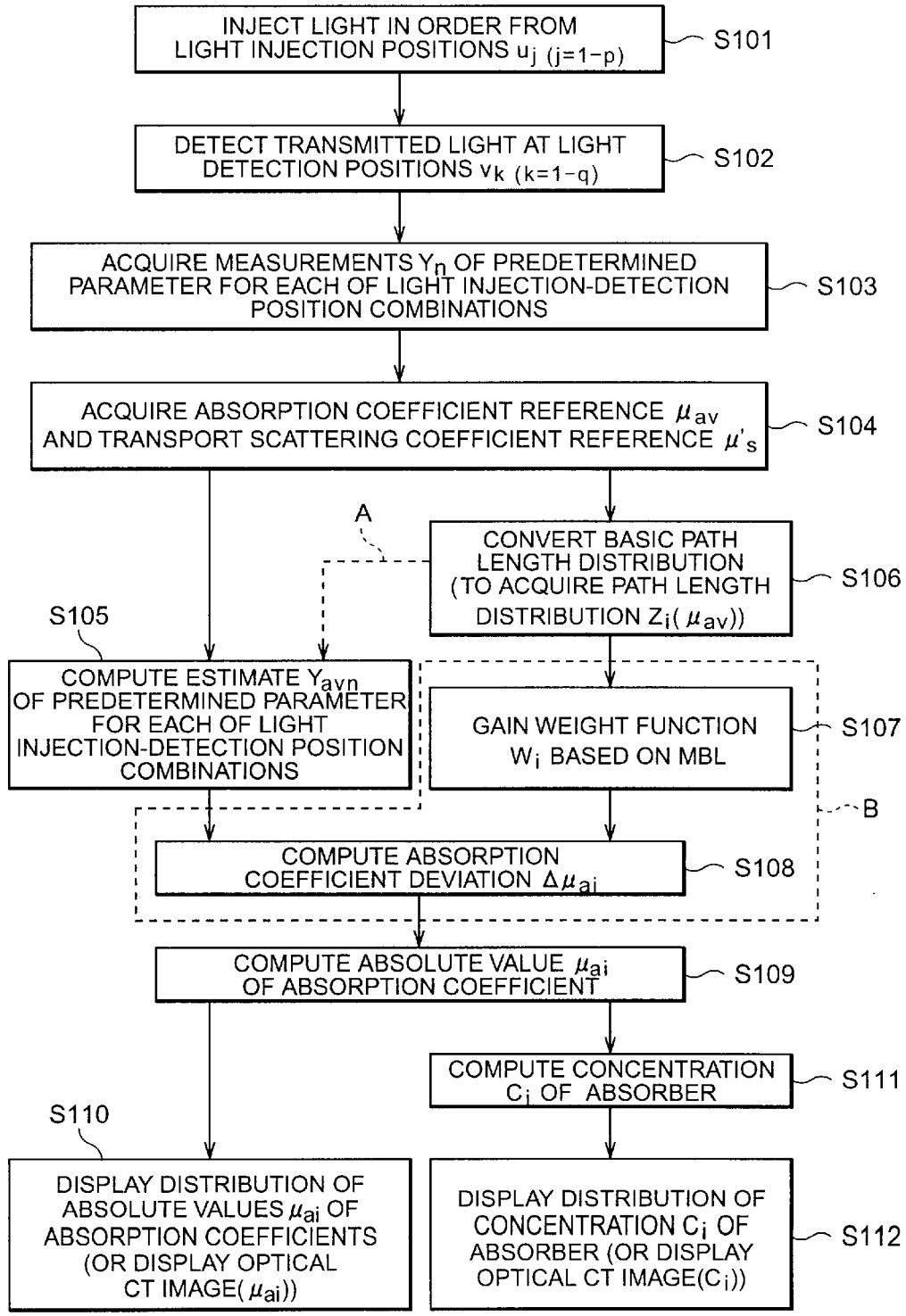
FIG. 3 is a flowchart to show an embodiment of the method for measuring an internal property distribution of a scattering medium according to the present invention.

1) In the flowchart illustrated in FIG. 3, the first step is to inject rays (light beams) generated in the light source 23, successively through the light injection fiber 21 at the different light injection positions $u_j$ (j=1 to p) into the measured medium 10 (S101), and the photodetectors 26 detect each ray having been scattered and transmitted inside the measured medium (which is part of the rays injected at each light injection position $u_j$) through the respective light detection fibers 25 located at the plurality of light detection positions $v_k$ (k=1 to q) (S102).

Then the photodetectors 26 generate light detection signals corresponding to rays detected at the plurality of light detection positions $v_k$ (k=1 to q) against the rays injected at each photon injection position $u_j$, and the CPU 30 converts them to measurement values $Y_n$ of the predetermined parameter of the detected rays. In this way the measurement values $Y_n$ of the predetermined parameter of the detected rays are obtained for each of the combinations $P_n$ of the light injection positions $u_j$ (j=1 to p) with the light detection positions $v_k$ (k=1 to q), and they are stored as n sets (n=p×q) of measured data in the measurement data file 52 (S103). On this occasion, the combinations $P_n$ of the light injection-detection positions to the n sets of data are different from each other.

The measurement values $Y_n$ of the predetermined parameter according to the present invention are preferably measurement values of a predetermined parameter related to scattering and absorption of the measurement rays inside the measured object, and, for example, suitably applicable measurement values are those of such parameters as the light quantity, phase difference (or phase lag), amplitude, time-resolved waveform, etc. of the detected rays. The CPU 30 can perform the time-resolved gate integration measurement if the integration operation of the light detection signals is carried out in a predetermined time range ($t_1 \rightarrow t_2$) by making use of signals timed with generation of the rays from the light source 23. On the other hand, it can also perform the ordinary time-resolved integration measurement if the integration range is set in $0 \rightarrow \infty$. In the case of the pulsed rays etc. being used, the synchronous signals do not have to be used. The CPU 30 may also be arranged to perform correction for the measurement values by making use of the averaging filtering, the least square fitting, or the like.

2) The next step is to set a reference value $\mu_{av}$ of the absorption coefficient and a reference value $\mu'_s$ of the transport scattering coefficient of the measured medium 10 (S104). The reference value $\mu_{av}$ of the absorption coefficient does not have to be equal to the true average absorption coefficient for the imaginary medium and may be approximated to $\mu_{av}=0$. In general, however, the measurement accuracy is apt to be higher when a value close to the true average absorption coefficient is used as $\mu_{av}$. It is thus preferable to employ, as the reference value $\mu_{av}$ of the absorption coefficient, an average absorption coefficient (approximate value) from a macroscopic aspect of the measured medium 10, i.e., that on the assumption that the measured medium 10 has the homogeneous absorption coefficient as a whole. Likewise, it is also preferable to employ, as the reference value $\mu'_s$ of the transport scattering coefficient, an average transport scattering coefficient (approximate value) on the assumption that the measured medium 10 has the homogeneous scattering coefficient as a whole.

Such absorption coefficient $\mu_{av}$ and transport scattering coefficient $\mu'_s$ can be obtained from the light detection signals (or the measurement values $Y_n$ of the predetermined parameter) detected at the aforementioned plurality of light detection positions $v_k$. For example, where the light detection signals are impulse responses (light detection signals against injection of pulsed light assumed to be sufficiently short relative to temporal waveforms of the light detection signals), the absorption coefficient $\mu_{av}$ and transport scattering coefficient Ats of the interior of the medium corresponding to a predetermined light injection-detection position combination $P_n$ can be obtained by fitting the temporal waveforms to the photon diffusion equation. Therefore, we can employ an average of absorption coefficients $\mu_{av}$ and an average of transport scattering coefficients $\mu'_s$ obtained corresponding to the respective light injection-detection position combinations $P_n$. Further, these values can be utilized in the time-resolved gate integration measurement and the phase modulation measurement. Such methods of acquiring the absorption coefficient $\mu_{av}$ and transport scattering coefficient $\mu'_s$ are described, for example, in the following references: (21) R. Berg, S. Andersson-Engels, O. Jarlman and S. Svanberg: Proc. SPIE, Vol. 1431, 110–119 (1991); (22) M. Miwa, Y. Ueda and B. Chance: Proc. SPIE, Vol. 2389, 142–149 (1995); (23) R. Cubeddu, A. Pifferi, P. Taroni, A. Torricelli and G. Valentini, Phy. Med. Biol. 42, 1971–1979 (1997).

On the occasion of setting the above reference values, another average optical constant may also be obtained further from the macroscopic aspect of the measured medium 10, and examples of such an optical constant include the refractive index $n_e$ of the measured medium, the scattering coefficient $\mu_s$, and the average cosine g of scattered angles. The refractive index $n_e$ of the measured medium can be normally approximated to that of water.

3) Next, on the assumption that the measured medium 10 has the homogeneous reference value $\mu_{av}$ of average coefficient as a whole, an estimate $Y_{avn}$ of the predetermined parameter is obtained for each of the combinations $P_n$ of the light injection positions with the light detection positions, based on the homogeneous reference value $\mu_{av}$ of the absorption coefficient (S105).

Namely, the estimate of the predetermined parameter (of the light detection signal) in each light injection-detection position combination $P_n$ can be yielded, for example, by solving the photon diffusion equation with provision of the above average optical constants (the reference value $\mu_{av}$ of the absorption coefficient, the reference value $\mu'_s$ of the transport scattering coefficient, etc.). There is also a developed method for estimating the result with change of an optical constant from the result of Monte Carlo calculation with provision of any given optical constant (for example, absorption coefficient) (for example, as described in A. Kienle and M. S. Patterson: Phys. Med. Biol. 41, 2221–2227 (1996)). Therefore, we can compute the estimate $Y_{avn}$ of the predetermined parameter (of the light detection signal) in each light injection-detection position combination $P_n$ by use of the reference value $\mu_{av}$ of the absorption coefficient from the result of such Monte Carlo calculation.

4) on the other hand, the mean path length $Z_i(\mu_{av})$ in each voxel i of the measured medium 10 divided into a plurality of voxels is acquired, based on the reference value $\mu_{av}$ of the absorption coefficient, on the assumption that the measured medium 10 has the homogeneous reference value $\mu_{av}$ of the absorption coefficient as a whole (S106).

In the present invention, it is necessary to gain the weight functions matching with measurement circumstances on the occasion of each of individual measurements, by the method described hereinafter. In this case, in view of the real time nature of measurement, it is necessary to obtain the weight functions in situ (upon the measurement) quickly. It is thus preferable to preliminarily prepare the common basic path length distribution as a basis for the operation of various weight functions used in various measurements and convert the basic path length distribution according to measurement circumstances upon measurement, which tends to enable the necessary weight functions to be gained quickly.

Therefore, the basic path length distribution preliminarily determined by the Monte Carlo calculation or the like is read out of the basic path length distribution data file 51 and, based on the reference value $\mu_{av}$ of the absorption coefficient and the reference value $\mu'_s$ of the transport scattering coefficient, the path length distribution of detected rays can be determined for the imaginary medium having th ese reference values. This is conversion of the basic path length distribution, which can be carried out using the method described in (24) A. Kienle and M. Patterson: Phys. Med. Biol. 41, 2221–2227 (1996), for example.

The estimate $Y_{avn}$ of the predetermined parameter (of the light detection signal) in each light injection-detection position combination $P_n$ can also be computed based on the path length distribution $Z_i(\mu_{av})$ of detected rays for the imaginary medium, obtained herein. A flow of processing in this case is indicated by a chain line A in FIG. 3.

5) Then, based on the mean path length $Z_i(\mu_{av})$ in each voxel i obtained using the reference value $\mu_{av}$ of the absorption coefficient as described above, the weight function $W_i$ in each voxel i is computed according to Eq. (4.6) in conformity with the Microscopic Beer-Lambert Law (S107), and then, based on the measurement values $Y_n$ and estimates $Y_{avn}$ of the predetermined parameter in the respective light injection-detection position combinations $P_n$ and the weight functions $W_i$, the deviation $\Delta\mu_{ai}$ of the absorption coefficient from the reference value $\mu_{av}$ of the absorption coefficient in each voxel i is computed according to Eq. (4.5) (S108).

The weight functions $W_i$ to be gained here are those indicated by Eq. (4.6) which is the following equation.

$$W_i=Z_i(\mu_{av})-(\Delta\mu_{ai}/2)\sigma_{iv}^2 \tag{c.1}$$

Figure 4:
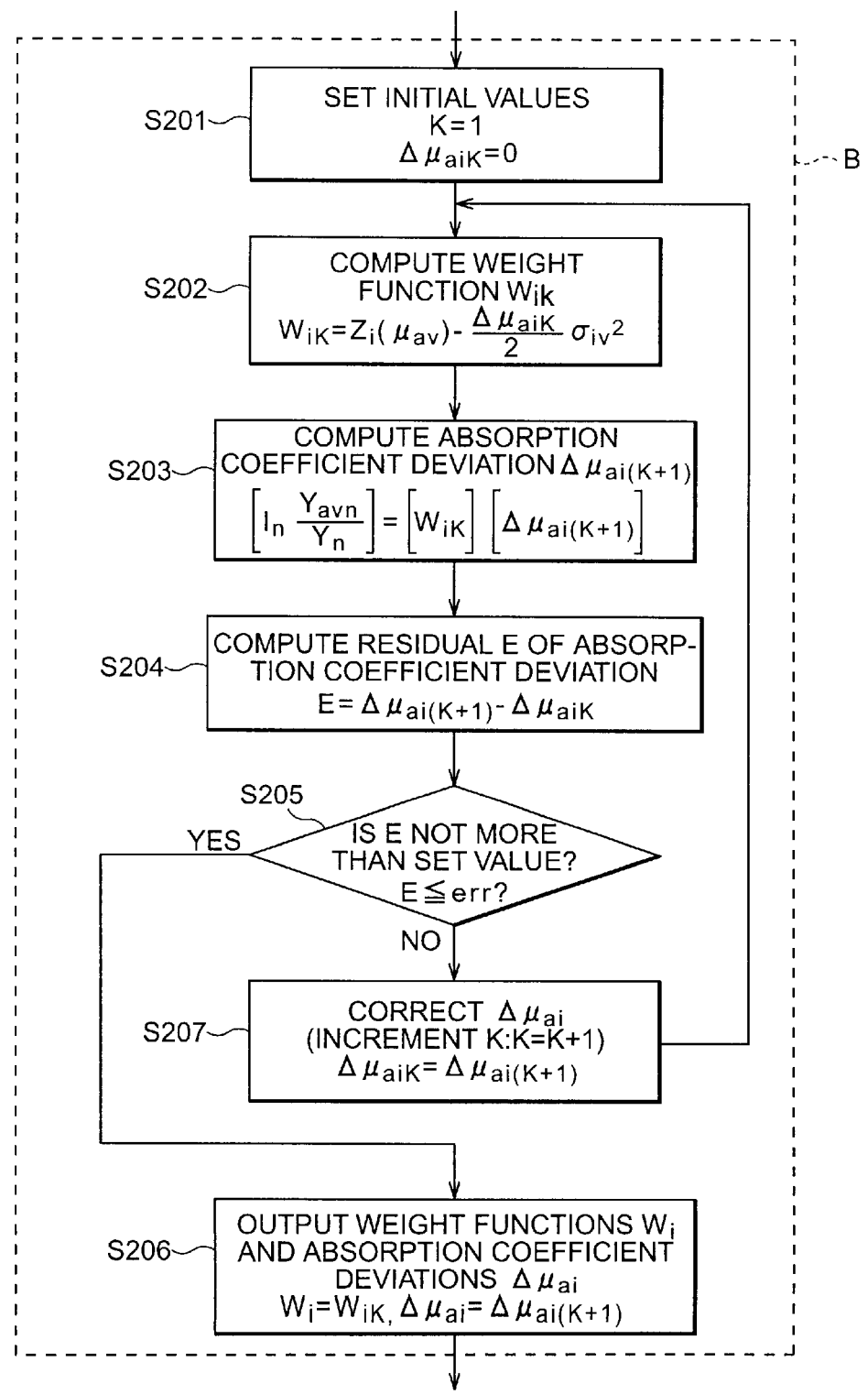
FIG. 4 is a flowchart to show an embodiment of an operation method for gaining the weight function according to the present invention.

It should be noted here that the weight function $W_i$ in each voxel needs to be a function of the absorption coefficient deviation $\Delta\mu_{ai}=\mu_{ai}-\mu_{av}$ (i=1 to N) of that voxel. It is thus preferable that such weight functions $W_i$ be acquired together with the absorption coefficient deviations $\Delta\mu_{ai}$ by iterative computations as described below. Namely, the operations of S107 and S108 (indicated by the chain line B in FIG. 3) are normally carried out repeatedly. FIG. 4 is a flowchart to show a preferred embodiment of the processing for obtaining the weight functions $W_i$ and absorption coefficient deviations $\Delta\mu_{ai}$ by such iterative operations. The flowchart illustrated in FIG. 4 will be detailed below.

First, an initial value of the order K is set to K=1 and an initial value of the absorption coefficient deviation $\Delta\mu_{ai}$ to $\Delta\mu_{aiK}=0$ (S201). Then the weight function $W_{iK}$ is determined according to Eq. (4.6), based on the mean path length $Z_i(\mu_{av})$ and absorption coefficient deviation $\Delta\mu_{aiK}$ in each voxel i (S202). Here $\sigma_{iv}^2$ in Eq. (4.6) represents the variance and is obtained, for example, by computation of Eq. (3.2.10) or Eq. (3.3.8).

Next, the deviation $\Delta\mu_{ai}$ (K+1) of the absorption coefficient in each voxel i is computed according to Eq. (4.5), based on the measurement values $Y_n$ and estimates $Y_{avn}$ of the predetermined parameter and the weight functions $W_{iK}$ (S203). Natural logarithms of ratios of aforementioned $Y_{avn}$ to $Y_n$, [$\ln(Y_{avn}/Y_n)$], correspond to $\Delta Y_n$ in Eq. (4.5).

Then a residual E is computed between the deviation $\Delta\mu_{ai}$(K+1) of the absorption coefficient obtained in S203 and the absorption coefficient deviation $\Delta\mu_{aiK}$ used in S202 (S204), and it is determined whether the value thereof is not more than a predetermined value (err) (S205).

As a result, when the above residual E is not more than the predetermined value, the weight functions $W_{iK}$ at that time are outputted as the weight functions $W_i$ and the absorption coefficient deviations $\Delta\mu_{ai}$(K+1) at that time as the absorption coefficient deviations $\Delta\mu_{ai}$ (S206). On the other hand, when the above residual E is more than the predetermined value, the absorption coefficient deviations $\Delta\mu_{aiK}$ used in S202 are replaced by the absorption coefficient deviations $\Delta\mu_{ai}$(K+1) gained in aforementioned S203 (an increment of 1 is given to the order K: S207), and the operation of the weight functions $W_{iK}$ (S202), the operation of the absorption coefficient deviations $\Delta\mu_{ai}$(K+1) (S203), and the operation of the aforementioned residual E (S204) are carried out again. It is then determined whether the residual E is not more than the predetermined value (err) (S205), and the above processing of S207→S202 →S203→S204→S205 is repeated until the residual E becomes not more than the predetermined value. Each of the above steps may be performed as follows: S201 by an initial value setting means; S202 by a weight function operation means; S203 by an absorption coefficient deviation operation means; S204, S205, and S206 by an evaluation means; and S207 by an absorption coefficient deviation correction means.

Figure 5:
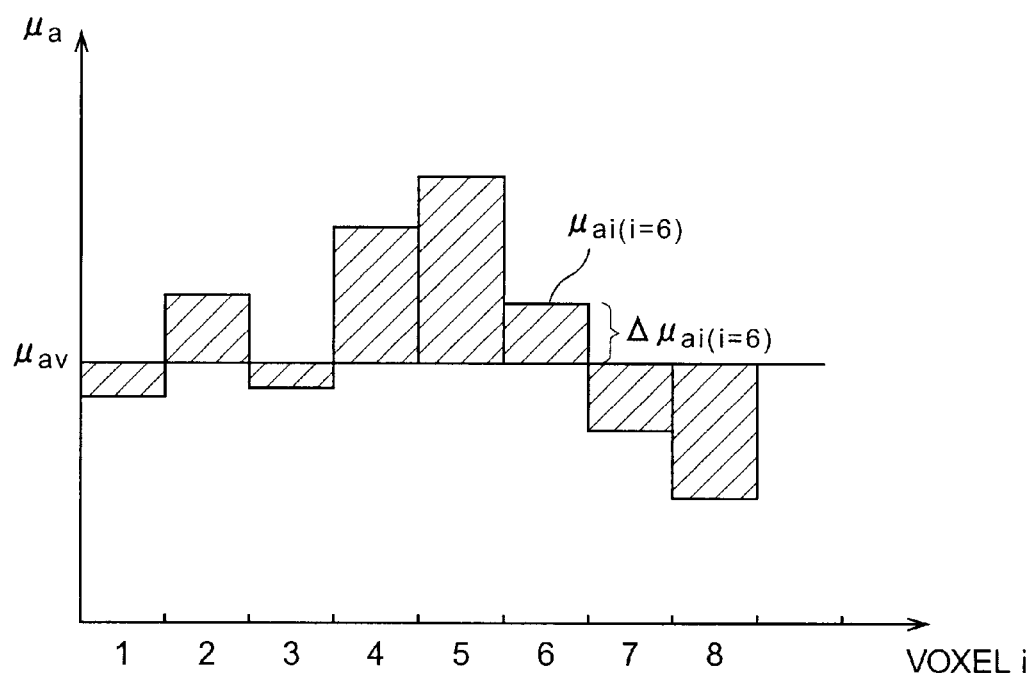
FIG. 5 is a graph to show an absorption coefficient distribution (a relation between reference value of absorption coefficient and deviation of absorption coefficient) in each voxel.

6) The above processing yields the distribution of absorption coefficient deviations (deviations of absorption coefficients in the respective voxels i) $\Delta\mu_{ai}=\mu_{ai}-\mu_{av}$ (i=1 to N). Here $\Delta\mu_{ai}$ indicates the deviations from the reference value of absorption coefficient (preferably, the average absorption coefficient) $\mu_{av}$ described previously. Therefore, the absolute value $\mu_{ai}$ of the absorption coefficient in each voxel i can be computed according to the following equation:

$$\mu_{ai}=\Delta\mu_{ai}+\mu_{av}(\text{i=1 to N}),$$

using the deviation $\Delta\mu_{ai}$ of the absorption coefficient in each voxel i and the reference value $\mu_{av}$ of the absorption coefficient (S109), and is then stored in the absorption coefficient data file 54. FIG. 5 shows the relationship among the reference value $\mu_{av}$, the deviations $\Delta\mu_{ai}$, and the absolute values $\mu_{ai}$ of absorption coefficients. Then a distribution concerning the absolute values of absorption coefficients in the interior of the measured medium is obtained based on the absolute value $\mu_{ai}$ of the absorption coefficient in each voxel i obtained as described above, and an optical CT image to indicate the distribution is displayed at the output device 80 (S110).

7) Next, let us describe a concentration operation of the absorptive component. Let us consider here an example in which the measured medium contains one kind of an absorptive constituent. Then, the concentration deviation $\Delta C_i$ of the absorber in the voxel i is given by the following equation derived from the Beer-Lambert Law:

$$\epsilon\Delta C_i=\mu_{ai}-\mu_{av} \tag{C.2}$$

In this equation $\epsilon$ indicates an absorption coefficient (or extinction coefficient) per unit concentration of the absorber, which can be measured by a spectrophotometer. Further, the concentration $C_i$ in each voxel i of the aforementioned absorber is given by the following equation derived from the Beer-Lambert Law;

$$\epsilon C_i=\mu_{ai} \tag{C.3}$$

Therefore, the concentration $C_i$ of the absorber in each voxel i can be computed from the above absolute value $\mu_{ai}$ of the absorption coefficient in each voxel i, using the known absorption coefficient of the absorber (S111), and is stored in the absorber concentration data file 55. Then a distribution concerning concentrations of the absorber in the interior of the measured medium is obtained based on the concentration $C_i$ of the absorber in each voxel i thus obtained, and an optical CT image to indicate the distribution is displayed at the output device 80 (S112).

(Second Embodiment)

Deviations and absolute values of concentrations of two or more kinds of absorbers can also be measured using rays of two or more wavelengths in the above method of the first embodiment. The present embodiment illustrates a two-wavelength spectroscopic measurement method for measurement with two types of rays of the wavelengths $\lambda_1$ and $\lambda_2$. Namely, if absorption coefficients (or extinction coefficients) $\epsilon_1$ and $\epsilon_2$ per unit concentration of each absorber corresponding to the rays of the wavelengths $\lambda_1$ and $\lambda_2$ are known, two equations hold as to aforementioned Eq. (C.2) and Eq. (C.3). $W_i$ the simultaneous system of these equations, it is thus possible to measure the deviations and absolute values of concentrations of the two types of absorbers.

More specifically, where a scattering medium contains at least two absorptive constituents (for example, oxygenated and deoxygenated hemoglobins), the distribution of concentrations $C_i$ of each absorptive constituent can be obtained by using the measurement rays having at least two wavelengths at which the absorptive constituents demonstrate their respective absorption coefficients different from each other, gaining the measurement values $Y_n$, estimates $Y_{avn}$, reference value $\mu_{av}$, and weight functions $W_i$ for each of the measurement rays having the respective wavelengths, and computing the absorption coefficient deviations $\Delta\mu_{ai}$ and absorption coefficient absolute values $\mu_{ai}$ for each of the measurement rays having the respective wavelengths, based thereon.

Figure 6:
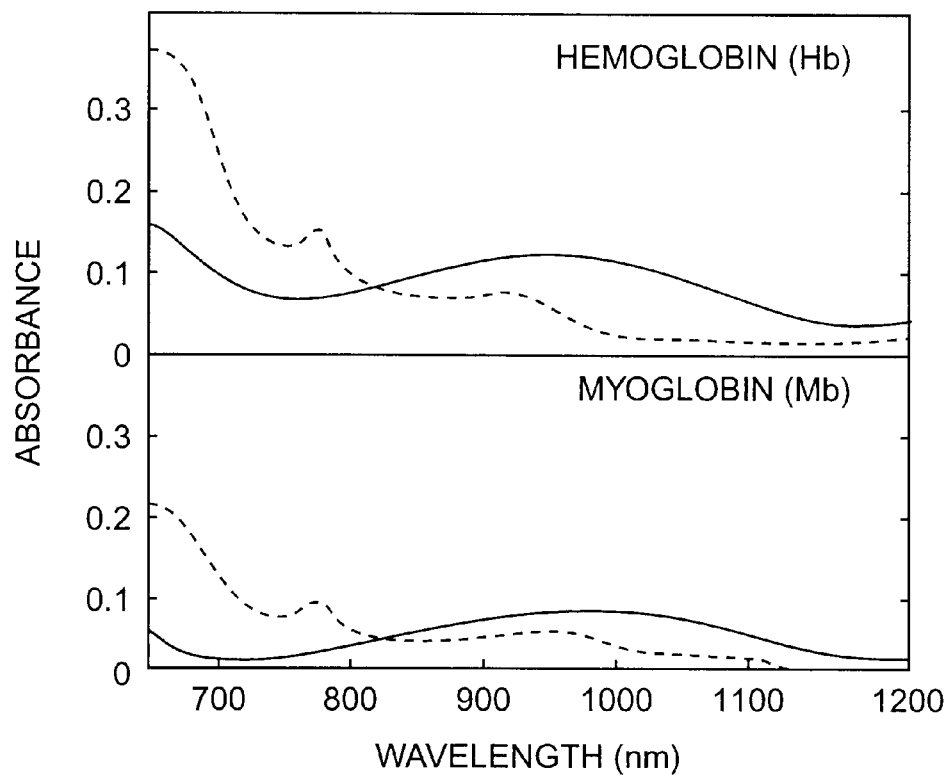
FIG. 6 is a graph to show absorption spectra of hemoglobin and myoglobin.

Now let us describe how to measure concentrations of hemoglobin by making use of the above two-wavelength spectroscopic method. The principal absorptive constituents in mammalian brain are water, cytochrome, and oxygenated and deoxygenated hemoglobins. Absorption of water and cytochrome in the near-infrared region is as little as almost negligible with respect to that of oxygenated and deoxygenated hemoglobins. The oxygenated and deoxygenated hemoglobins demonstrate different absorption spectra, as illustrated in FIG. 6. Further, the cranial bones can be considered to be scattering media against near-infrared rays.

Supposing that the absorption coefficients $\mu_{a1}$ and $\mu_{a2}$ were obtained for the rays of the two types of wavelengths, the wavelengths $\lambda_1$ and $\lambda_2$, by the methods discussed in the previous sections, the following equations hold in accordance with the Lambert-Beer Law.

$$\mu_{a1} = \epsilon_{Hb,1}[Hb] + \epsilon_{HbO,1}[HbO]$$

$$\mu_{a2} = \epsilon_{Hb,2}[Hb] + \epsilon_{HbO,2}[HbO]$$

where $\epsilon_{Hb,1}$: molar absorption coefficient [mm$^{-1}$.M$^{-1}$] of deoxygenated hemoglobin at wavelength $\lambda_1$;

$\epsilon_{HbO,1}$: molar absorption coefficient [mm$^{-1}$.M$^{-1}$] of oxygenated hemoglobin at wavelength $\lambda_1$;

$\epsilon_{Hb,2}$: molar absorption coefficient [mm$^{-1}$.M$^{-1}$] of deoxygenated hemoglobin at wavelength $\lambda_2$;

$\epsilon_{HbO,2}$: molar absorption coefficient [mm$^{-1}$.M$^{-1}$] of oxygenated hemoglobin at wavelength $\lambda_2$;

[Hb]: molar concentration [M] of deoxygenated hemoglobin;

[HbO]: molar concentration [M] of oxygenated hemoglobin.

Therefore, the molar concentration [Hb] of deoxygenated hemoglobin and the molar concentration [HbO] of oxygenated hemoglobin can be acquired from the known parameters $\epsilon_{Hb,1}$, $\epsilon_{HbO,1}$, $\epsilon_{Hb,2}$, $\epsilon_{HbO,2}$ and the values $\mu_{a1}$ and $\mu_{a2}$ computed from the measurement values.

For taking cytochrome into consideration in the above case, rays of three or more wavelengths can be used for quantitation of concentrations of the three components whose absorption spectra are known. In general, quantitation of concentrations of n components whose absorption spectra are known, can be implemented in similar fashion to the above, from measurement values of absorption coefficients at n or (n+1) wavelengths.

Further, since the degree of saturation Y is defined as follows:

$$Y = [HbO]/([Hb]+[HbO]),$$

the saturation degree Y can be computed readily from the known parameters $\epsilon_{Hb,1}$, $\epsilon_{HbO,1}$, $\epsilon_{Hb,2}$, $\epsilon_{HbO,2}$ and the values $\mu_{a1}$ and $\mu_{a2}$ computed from measurement values, using the following equation.

$$\mu_{a1}/\mu_{a2} = [\varepsilon_{Hb,1} + Y(\varepsilon_{HbO,1} - \varepsilon_{Hb,1})] \div [\varepsilon_{Hb,2} + Y(\varepsilon_{HbO,2} - \varepsilon_{Hb,2})]$$

Since the above method provides the absorption coefficients $\mu_{a1}$ and $\mu_{a2}$ with high accuracy against the rays of the respective wavelengths according to the present invention, each of the concentrations can also be gained with high accuracy. It is also noted that the above equation will be simplified further by use of the wavelength (800 nm isosbestic wavelength) at which the oxygenated and deoxygenated hemoglobins demonstrate an equal absorption value.

(Third Embodiment)

The present embodiment illustrates an example of application of the present invention to the phase modulation measurement. In this case, the measurement values $Y_n$, estimates $Y_{avn}$, reference value $\mu_{av}$, and weight functions $W_i$ are obtained in the same manner as in the first embodiment except that the incident rays in the first embodiment are replaced by amplitude-modulated rays, the predetermined parameter by the amplitude A and phase lag $\phi$ of detected rays, the path length distribution $Z_i(\mu_{av})$ of detected rays by a distribution of c (the speed of light in the medium) times group delay defined below:

$$c\left.\frac{\partial \phi_i}{\partial \omega}\right|_{\mu_{av}};$$

and $\sigma_{iv}^2$ by the variance, and the absorption coefficient deviations $\Delta\mu_{ai}$ and absolute values $\mu_{ai}$ of absorption coefficients are determined based thereon, thereby obtaining the distribution of concentrations $C_i$ of the absorptive constituent.

In this case, the weight functions $W_i$ to be obtained were those represented by the following equation:

$$W_i = c\left.\frac{\partial \phi_i}{\partial \omega}\right|_{\mu_{av}} - \frac{\Delta\mu_{ai}}{2}\sigma_f^2 \qquad (2)$$

and $\sigma_f^2$ indicates the variance of the distribution. Further, the basic path length distribution in the first embodiment is replaced by the c times group delay distribution.

The preferred embodiments of the present invention have been described heretofore, but it should be noted that the present invention is by no means intended to be limited to the above embodiments.

For example, the reference value of absorption coefficient and the reference value of transport scattering coefficient were determined from the data acquired by the optical CT system itself in the above embodiments, but these reference values may also be acquired by another device. An advantage in this case is a simpler system configuration of the optical CT apparatus, because it permits the data acquired by the optical CT apparatus to be measured with CW (continuous rays) and also permits the pulsed rays or modulated rays to be used only in the device for acquiring the above reference values. Techniques for attaining the above reference values by another device may be the phase modulation method and the time-resolved spectroscopy.

In the above embodiments the apparatus was arranged to move the light injection position, but the apparatus may also be modified so as to move the light detection position in synchronism with the light injection position. The apparatus may also be modified in such structure that a plurality of light injection fibers and a plurality of light detection fibers are arranged around the measured medium and that the light injection position is moved by successively selecting the fibers used for injection of light.

Further, it is obvious that the apparatus and methods of the present invention described above can also be applied to apparatus and methods for three-dimensionally measuring an absorptive constituent inside a three-dimensional medium, without having to be limited to the optical CT for obtaining ordinary tomographic images. It is also obvious that the apparatus and methods of the present invention can be applied to measurement of media having laminar structure of many layers, such as the head skin, cranial bones, gray matter, and white matter. In this case, the layers can be considered in correspondence to the respective voxels.

As described above, the present invention allows the weight functions in the respective voxels to be gained directly based on the Microscopic Beer-Lambert Law in each of individual measurements by use of the new weight functions and thus allows the deviations of absorption coefficients to be computed based on the proper weight functions according to the measurement circumstances, thereby preventing the rise of errors due to employment of approximation. For that reason, the present invention enables the deviations of absorption coefficients in the voxels to be gained accurately even when applied to the scattering media of such inhomogeneous systems as organisms and also enables the highly accurate internal property distribution to be gained based on such absorption coefficient deviations and to be imaged as an optical CT image.

As described, the present invention enables the distribution of an absorber or absorbers in the interior of various scattering media having various contours permitting no reentry of light to be measured with high accuracy and quickly, and can also be applied, for example, to photo-mammography, optical CT of head, optical CT for the entire body, clinical monitors, diagnosis and analysis, and operations and cures.

What is claimed is:

1. A method of measuring an internal property distribution of a scattering medium, said method comprising:

a light injection step of successively injecting rays from at least one light injection position into a medium to be measured, which is a scattering medium;

a light detection step of detecting rays having passed through the interior of said medium to be measured, at a plurality of light detection positions;

a measurement value acquisition step of acquiring a measurement value of a predetermined parameter of said rays for each of combinations of said light injection position with said light detection positions, based on each ray detected;

a reference value setting step of setting a reference value of an absorption coefficient of said medium to be measured;

an estimate computation step of computing an estimate of said parameter for each of the combinations of said light injection position with said light detection positions, based on said reference value of the absorption coefficient, on the assumption that said medium to be measured has the homogeneous reference value of said absorption coefficient as a whole;

a weight function operation step of obtaining a weight function in each voxel of said medium to be measured, the medium being divided into a plurality of voxels, based on the Microscopic Beer-Lambert Law, using said reference value of the absorption coefficient;

an absorption coefficient deviation computation step of computing a deviation of the absorption coefficient from the reference value of the absorption coefficient in each voxel, based on the measurement value of said parameter, the estimate of said parameter, and said weight function; and an absorption coefficient absolute value computation step of computing an absolute value of the absorption coefficient in each voxel, based on the reference value of said absorption coefficient and the deviation of said absorption coefficient, to obtain a distribution of absolute values of absorption coefficients in said medium to be measured.

2. The method according to claim 1, wherein said weight function is a function of a mean path length in each voxel and a variance of a distribution of path lengths, on the assumption that said medium to be measured has the homogeneous reference value of said absorption coefficient as a whole.

3. The method according to claim 2, further comprising a mean path length acquisition step of acquiring a mean path length in each voxel, based on the reference value of said absorption coefficient, on the assumption that said medium to be measured has the homogeneous reference value of said absorption coefficient as a whole, wherein said weight function operation step comprises a step of gaining said weight function, based on the following equation:

$$W_i = Z_i(\mu_{av}) - (\Delta\mu_{ai}/2)\sigma_{iv}^2 \qquad (1)$$

where $W_i$ is the weight function, $Z_i(\mu_{av})$ the mean path length, $\Delta\mu_{ai}$ the deviation of the absorption coefficient, and $\sigma_{iv}^2$ the variance of the distribution of path lengths.

4. The method according to claim 1, wherein said weight function is a function of a mean path length in a predetermined time domain in each voxel and a variance of a distribution of path lengths, on the assumption that said medium to be measured has the homogeneous reference value of said absorption coefficient as a whole.

5. The method according to claim 4, further comprising a mean path length acquisition step of acquiring a mean path length in a predetermined time domain in each voxel, based on the reference value of said absorption coefficient, on the assumption that said medium to be measured has the homogeneous reference value of said absorption coefficient as a whole, wherein said weight function operation step comprises a step of gaining said weight function, based on the following equation:

$$W_i = Z_i(\mu_{av}) - (\Delta\mu_{ai}/2)\sigma_{iv}^2 \qquad (1)$$

6. The method according to claim 1, wherein said weight function is a function of a group delay in each voxel and a variance of a distribution thereof, on the assumption that said medium to be measured has the homogeneous reference value of said absorption coefficient as a whole.

7. The method according to claim 6, further comprising a group delay acquisition step of acquiring a group delay in each voxel, based on the reference value of said absorption coefficient, on the assumption that said medium to be measured has the homogeneous reference value of said absorption coefficient as a whole, wherein said weight function operation step comprises a step of gaining said weight function, based on the following equation:

$$W_i = c \left.\frac{\partial \phi_i}{\partial \omega}\right|_{\mu_{av}} - \frac{\Delta \mu_{ai}}{2} \sigma_f^2 \qquad (2)$$

where $W_i$ is the weight function, $$c \left.\frac{\partial \phi_i}{\partial \omega}\right|_{\mu_{av}}$$

is c (speed of light in the medium) times the group delay, $\Delta\mu_{ai}$ the deviation of the absorption coefficient, and $\sigma_f^2$ the variance of a distribution.

8. The method according to claim 1, further comprising a concentration computation step of computing a concentration of an absorptive constituent in each voxel by using an absolute value of said absorption coefficient, and thus obtaining a concentration distribution of the absorptive constituent in said medium to be measured.

9. The method according to claim 8, wherein said medium to be measured contains at least two absorptive constituents,
wherein the rays injected into said medium to be measured in said light injection step have at least two wavelengths at which said absorptive constituents demonstrate respective absorption coefficients different from each other,
wherein said light detection step comprises a step of detecting each of the rays having said at least two wavelengths,
wherein said measurement value acquisition step comprises a step of acquiring said measurement value as to each of the rays having said at least two wavelengths,
wherein said reference value setting step comprises a step of setting said reference value as to each of the rays having said at least two wavelengths,
wherein said estimate computation step comprises a step of computing said estimate as to each of the rays having said at least two wavelengths,
wherein said weight function operation step comprises a step of gaining said weight function as to each of the rays having said at least two wavelengths,
wherein said absorption coefficient deviation computation step comprises a step of computing said deviation of the absorption coefficient as to each of the rays having said at least two wavelengths,
wherein said absorption coefficient absolute value computation step comprises a step of computing the absolute value of the absorption coefficient as to each of the rays having said at least two wavelengths, and
wherein said concentration computation step comprises a step of computing concentrations of each said absorptive constituents as to each of the rays having said at least two wavelengths to obtain distributions of concentrations of said respective absorptive constituents in said medium to be measured.

10. The method according to claim 1, further comprising an image display step of displaying an optical CT image to indicate the distribution in said medium to be measured, based on said distribution acquired.

11. An apparatus for measuring an internal property distribution of a scattering medium, said apparatus comprising:

light injection means for successively injecting rays from at least one light injection position into a medium to be measured, which is a scattering medium;
light detection means for detecting rays having passed through the interior of said medium to be measured, at a plurality of light detection positions;
measurement value acquisition means for acquiring a measurement value of a predetermined parameter of said rays for each of combinations of said light injection position with said light detection positions, based on each ray detected;
reference value setting means for setting a reference value of an absorption coefficient of said medium to be measured;
estimate computation means for computing an estimate of said parameter for each of the combinations of said light injection position with said light detection positions, based on said reference value of the absorption coefficient, on the assumption that said medium to be measured has the homogeneous reference value of said absorption coefficient as a whole;
weight function operation means for obtaining a weight function in each voxel of said medium to be measured, the medium being divided into a plurality of voxels, based on the Microscopic Beer-Lambert Law, using said reference value of the absorption coefficient;
absorption coefficient deviation computation means for computing a deviation of the absorption coefficient from the reference value of the absorption coefficient in each voxel, based on the measurement value of said parameter, the estimate of said parameter, and said weight function; and
absorption coefficient absolute value computation means for computing an absolute value of the absorption coefficient in each voxel, based on the reference value of said absorption coefficient and the deviation of said absorption coefficient, to obtain a distribution of absolute values of absorption coefficients in said medium to be measured.

12. The apparatus according to claim 11, wherein said weight function is a function of a mean path length in each voxel and a variance of a distribution of path lengths, on the assumption that said medium to be measured has the homogeneous reference value of said absorption coefficient as a whole.

13. The apparatus according to claim 12, further comprising mean path length acquisition means for acquiring a mean path length in each voxel, based on the reference value of said absorption coefficient, on the assumption that said medium to be measured has the homogeneous reference value of said absorption coefficient as a whole,
wherein said weight function operation means performs a step of gaining said weight function, based on the following equation:

$$W_i = Z_i(\mu_{av}) - (\Delta\mu ai/2)\sigma_{iv}^2 \qquad (1)$$

where $W_i$ is the weight function, $Z_i(\mu_{av})$ the mean path length, $\Delta\mu_{ai}$ the deviation of the absorption coefficient, and $\sigma_{iv}^2$ the variance of the distribution of path lengths.

14. The apparatus according to claim 11, wherein said weight function is a function of a mean path length in a predetermined time domain in each voxel and a variance of a distribution of path lengths, on the assumption that said medium to be measured has the homogeneous reference value of said absorption coefficient as a whole.

15. The apparatus according to claim 14, further comprising mean path length acquisition means for acquiring a mean path length in a predetermined time domain in each voxel, based on the reference value of said absorption coefficient, on the assumption that said medium to be measured has the homogeneous reference value of said absorption coefficient as a whole, wherein said weight function operation means performs a step of computing said weight function, based on the following equation:

$$W_i = Z_i(\mu_{av}) - (\Delta\mu_{ai}/2)\sigma_{iv}^2 \quad (1)$$

where $W_i$ is the weight function, $Z_i(\mu_{av})$ the mean path length, $\Delta\mu_{ai}$ the deviation of the absorption coefficient, and $\sigma_{iv}^2$ the variance of the distribution of path lengths.

16. The apparatus according to claim 11, wherein said weight function is a function of a group delay in each voxel and a variance of a distribution thereof, on the assumption that said medium to be measured has the homogeneous reference value of said absorption coefficient as a whole.

17. The apparatus according to claim 16, further comprising group delay acquisition means for acquiring a group delay in each voxel, based on the reference value of said absorption coefficient, on the assumption that said medium to be measured has the homogeneous reference value of said absorption coefficient as a whole, wherein said weight function operation means performs a step of gaining said weight function, based on the following equation:

$$W_i = c \left.\frac{\partial \phi_i}{\partial \omega}\right|_{\mu_{av}} - \frac{\Delta\mu_{ai}}{2} \sigma_f^2 \quad (2)$$

where $W_i$ is the weight function, $$c \left.\frac{\partial \phi_i}{\partial \omega}\right|_{\mu_{av}}$$

is c (speed of light in the medium) times the group delay, $\Delta\mu_{ai}$ the deviation of the absorption coefficient, and $\sigma_f^2$ the variance of a distribution.

18. The apparatus according to claim 11, further comprising concentration computation means for computing a concentration of an absorptive constituent in each voxel by using an absolute value of said absorption coefficient, and thus obtaining a concentration distribution of the absorptive constituent in said medium to be measured.

19. The apparatus according to claim 18, wherein said medium to be measured contains at least two absorptive constituents, wherein the rays injected into said medium to be measured by said light injection means have at least two wavelengths at which said absorptive constituents demonstrate respective absorption coefficients different from each other, wherein said light detection means performs a step of detecting each of the rays having said at least two wavelengths, wherein said measurement value acquisition means performs a step of acquiring said measurement value as to each of the rays having said at least two wavelengths, wherein said reference value setting means performs a step of setting said reference value as to each of the rays having said at least two wavelengths, wherein said estimate computation means performs a step of computing said estimate as to each of the rays having said at least two wavelengths, wherein said weight function operation means performs a step of gaining said weight function as to each of the rays having said at least two wavelengths, wherein said absorption coefficient deviation computation means performs a step of computing said deviation of the absorption coefficient as to each of the rays having said at least two wavelengths, wherein said absorption coefficient absolute value computation means performs a step of computing the absolute value of the absorption coefficient for each of the rays having said at least two wavelengths, and wherein said concentration computation means performs a step of computing concentrations of each said absorptive constituents as to each of the rays having said at least two wavelengths to obtain distributions of concentrations of said respective absorptive constituents in said medium to be measured.

20. The apparatus according to claim 11, further comprising image display means for displaying an optical CT image to indicate the distribution in said medium to be measured, based on said distribution acquired.

* * * * *